United States Patent
Dadachova et al.

(10) Patent No.: US 8,586,090 B2
(45) Date of Patent: Nov. 19, 2013

(54) MELANIN NANOSHELLS FOR PROTECTION AGAINST RADIATION AND ELECTRONIC PULSES

(75) Inventors: Ekaterina Dadachova, Mahopac, NY (US); Arturo Casadevall, New Rochelle, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 810 days.

(21) Appl. No.: 11/732,130

(22) Filed: Apr. 2, 2007

(65) Prior Publication Data

US 2007/0237829 A1  Oct. 11, 2007

Related U.S. Application Data

(63) Continuation-in-part of application No. PCT/US2005/035707, filed on Oct. 3, 2005.

(60) Provisional application No. 60/819,992, filed on Jul. 10, 2006, provisional application No. 60/616,056, filed on Oct. 5, 2004.

(51) Int. Cl.
*A61K 9/14* (2006.01)

(52) U.S. Cl.
USPC ............... 424/489; 424/195.15; 424/195.16; 424/780; 600/1

(58) Field of Classification Search
USPC ............................................ 435/170, 171, 41
See application file for complete search history.

(56) References Cited

U.S. PATENT DOCUMENTS

| | | | |
|---|---|---|---|
| 4,806,360 A | 2/1989 | Leong et al. | |
| 4,855,144 A | 8/1989 | Leong et al. | |
| 5,036,115 A | 7/1991 | Gallas | |
| 5,047,447 A | 9/1991 | Gallas | |
| 5,057,325 A * | 10/1991 | Montefiori | 424/522 |
| 5,066,082 A | 11/1991 | Longstaff | |
| 5,112,883 A | 5/1992 | Gallas | |
| 5,286,979 A | 2/1994 | Berliner et al. | |
| 5,380,359 A | 1/1995 | Honda et al. | |
| 5,801,047 A | 9/1998 | Della-Cioppa et al. | |
| 5,874,029 A * | 2/1999 | Subramaniam et al. | 264/12 |
| 5,954,871 A | 9/1999 | Nicolas-Morgantini et al. | |
| 6,034,003 A | 3/2000 | Lee | |
| 6,217,914 B1 | 4/2001 | Meisner | |
| 6,300,057 B1 * | 10/2001 | Garger et al. | 435/5 |
| 6,465,440 B2 | 10/2002 | von Borstel | |
| 6,509,325 B1 * | 1/2003 | Nosanchuk et al. | 514/109 |
| 6,576,268 B2 | 6/2003 | Kerestes, Jr. et al. | |
| 7,402,385 B2 | 7/2008 | Dadachova et al. | |
| 2002/0001565 A1 * | 1/2002 | Shapiro | 424/1.11 |
| 2003/0082232 A1 * | 5/2003 | Lee et al. | 424/484 |
| 2003/0086904 A1 * | 5/2003 | Rasmussen et al. | 424/93.2 |
| 2004/0115203 A1 | 6/2004 | Dadachova et al. | |
| 2004/0231719 A1 * | 11/2004 | Meredith | 136/263 |
| 2006/0039858 A1 | 2/2006 | Dadachova et al. | |
| 2006/0135427 A1 * | 6/2006 | Hays et al. | 514/12 |
| 2008/0226548 A1 | 9/2008 | Dadachova et al. | |

FOREIGN PATENT DOCUMENTS

WO   WO 2007/117453 A2   10/2007

OTHER PUBLICATIONS

Mosse, I et al. Melanin decreases clastogenic effects of ionizing radiation in human and mouse somatic cells and modifies the radioadaptive response. Radiat Environ Biophys. 2000. 39:47-52.*
Moghimi, SM. Prolonging the circulation time and modifying the body distribution of intravenously injected polystyrene nanospheres by prior intravenous administration of poloxamine-908. A 'hepatic-blockade' event or manipulation of nanosphere surface in vivo? Biochimica et Biophysica Acta. 1997. 1336: 1-6.*
International Search Report and Written Opinion in connection with PCT Patent Application No. PCT/US2005/35707 filed Oct. 3, 2005 (9 pgs).
Grossi GF et al. Effects of melanin on high-and low-linear energy transfer (LET) radiation response of human epithelial cells. Radiat Environ Biophys 37:63-67, 1998.
Schweitzer AD et al. Melanin-Covered Nanoparticles for Protection of Bone Marrow During Radiation Therapy of Cancer. Int J Radiat Oncol Biol. Phys. Epub Apr. 24, 2010, pp. 1-9.
Vasilevskaia A I et al., entitled "The dynamics of the fungal mycelial content in the soils of stationary posts in a 30-kilometer zone around the Chernobyl Atomic Electric Power Station," Mikrobiol Z, Jun.-Aug. 1993;55(4):8-15, Abstract Only.
Mironenko N V et al., entitled "Intraspecific varation in gamma-radiation resistance and genomic structure in the filamentous fungus *Alternaria alternata*: a case study of strains inhabiting Chernobyl reactor No. 4," Ecotoxicol Environ Saf., Feb. 2000;45(2):177-187, Abstract Only.
Dadchova E et al., entitled "Ionizing Radiation Changes the Electronic Properties of Melanin and Enhances the Growth of Melanized Fungi," Plos One, 2007, Issue 5, e457, 1-13.
Dadchova E et al., entitled "Susceptibility of the Human Pathogenic Fungi *Cryptococcus neoformans* and *Histoplasma capsulatum* to Gamma-Radiation Versus Radioimmunotherapy with Alpha- and Beta-Emitting Radioisotopes," J Nucl Med, 2004; 45:313-320.
Hill, H Z, entitled "The Function of Melanin or Six Blind People Examine an Elephant," BioEssays, vol. 14, No. 1, Jan. 1992, 49-56.
Hill, H Z et al., entitled "Ability of Melanins to Protect Against the Radiolysis of Thymine and Thymidine," Pigment Cell Research 1:81-86, 1987.
Kinnaert E et al., entitled "The Degree of Pigmentation Modulates the Radiosensitivity of Human Melanoma Cells," Radiation Research, 154, 497-502, 2000.
Nosanchuk, J D et al., entitled "The contribution of melanin to microbial pathogenesis," Cellular Microbiology, 2003, 5(4):203-223.

(Continued)

*Primary Examiner* — Allison Ford
*Assistant Examiner* — Susan E Fernandez
(74) *Attorney, Agent, or Firm* — Amster, Rothstein & Ebenstein LLP

(57) ABSTRACT

This invention provides melanin nanoshells and their use for protection against radiation, particularly ionizing radiation, and electronic pulses, and methods of making materials comprising melanin nanoshells.

18 Claims, 20 Drawing Sheets

(56) References Cited

OTHER PUBLICATIONS

Rofstad E K, entitled "Radiation Biology of Malignant Melanoma," Acta Radiologica, vol. 25, Fasc. 1, Jan.-Feb. 1986, 1-10.

Scott M C, et al., entitled "Human melanocortin 1 receptor variants, receptor function and melanocyte response to UV radiation,"Journal of Cell Science, 115 (11), 2002, 2349-2355.

Steenberger J N et al., entitled "*Cryptococcus neoformans* interactions with amoebae suggest an explanation for its virulence and intracellular pathogenic strategy in macrophages," PNAS, Dec. 18, 2001, vol. 98, No. 26, 15245-15250.

Wang Y et al., entitled "Melanin, Melanin "Ghosts," and Melanin Composition in *Cryptococcus neoformans*," Infection and Immunity, Jul. 1996, p. 2420-2424.

Wang Y et al., entitled "Decreased Susceptibility of Melanized *Cryptococcus neoformans* to UV Light," Applied and Environmental Microbiology, Oct. 1994, p. 3864-3866.

PCT International Preliminary Report on Patentability, issued by The International Bureau of WIPO, dated Mar. 17, 2009, in connection with PCT International Patent Application No. PCT/US2005/035707, 4 pages, Mar. 17, 2009.

\* cited by examiner

A)  B)

C)

C)

D)

A)

B)

C)

D)

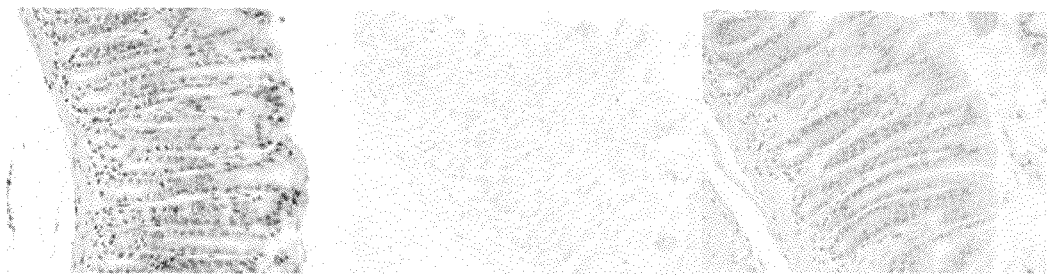
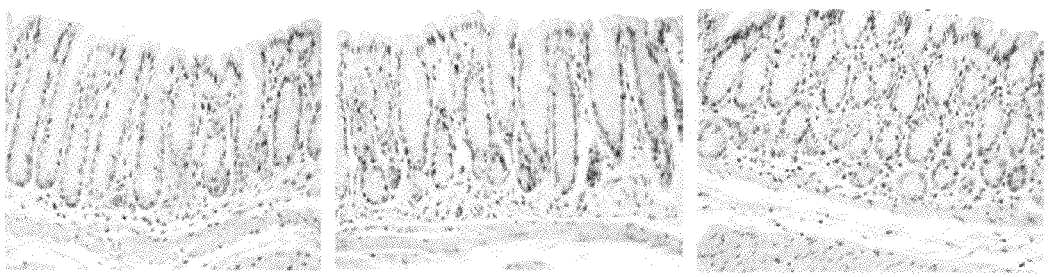
Figure 16A-16F

US 8,586,090 B2

MELANIN NANOSHELLS FOR PROTECTION AGAINST RADIATION AND ELECTRONIC PULSES

CROSS-REFERENCE TO RELATED APPLICATIONS

This application is a continuation-in-part of and claims priority of U.S. Provisional Patent Application No. 60/819,992, filed Jul. 10, 2006, and PCT International Patent Application No. PCT/US2005/035707, filed Oct. 3, 2005, which designates the United States of America and claims priority of U.S. Provisional Patent Application No. 60/616,056, filed Oct. 5, 2004, the contents of all of which are hereby incorporated by reference in their entirety into the subject application.

STATEMENT OF GOVERNMENT SUPPORT

The invention disclosed herein was made with U.S. Government support under grant number R21 AI52042 from the National Institutes of Health, U.S. Department of Health and Human Services. Accordingly, the U.S. Government has certain rights in this invention.

FIELD OF THE INVENTION

The present invention relates to melanin-based nanoshells and their use for protection against radiation, particularly ionizing radiation, and electronic pulses, and to methods of making materials comprising the melanin nanoshells.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Melanin is a high molecular weight pigment that is ubiquitous in nature and has a variety of biological functions (1). Melanins are found in all biological kingdoms. These pigments are among the most stable, insoluble, and resistant of biological materials (30). Melanins can have different structures depending on the biosynthetic pathway and precursor molecules. Some definitions of melanin have focused on chemical and physical properties of melanins instead of defined structures (29). Melanins can be synthesized in the laboratory by chemical means or by many living organisms. Melanins formed by the oxidative polymerization of phenolic compounds are usually dark brown or black (30). However, melanins may have other colors as illustrated by the finding that dopamine-derived melanin is reddish-brown. Fungi can make melanins from at least two major biosynthetic pathways, employing the precursor 1,8-dihydroxynapthalene (DHN melanin) or the oxidation of suitable tyrosine derivatives like dihydroxyphenylalanine (DOPA-melanin) (30). The fungus C. neoformans can make melanins from a wide variety of phenolic compounds which are oxidized by a laccase enzyme (31-33).

Melanins protect against UV light by absorbing a broad range of the electromagnetic radiation (1), and the melanin pigment is used in photo-protective creams (10). The presence of melanin is implicated in the resistance of human malignant pigmented melanoma to radiation therapy (9). Many fungi constitutively synthesize melanin (2). The ability of free-living microorganisms to make melanin may be associated with a survival advantage in the environment (3) that includes protection against solar radiation (reviewed in 4). Melanized fungi are also resistant to ionizing radiation (5). An example of such radiation resistance is provided by reports that melanized fungi colonize the walls of the damaged nuclear reactor in Chernobyl (6). The soils around the damaged reactor have blackened as the resident flora changes to include disproportionately more melanotic fungi (7). Water in nuclear reactor cooling pools is sometimes contaminated with melanized microorganisms (8). However, despite the finding of melanotic organisms in such harsh environments, the contribution of melanin to the radiation resistance of these organisms is uncertain.

SUMMARY OF THE INVENTION

The present invention is directed to nanoshells comprising melanin.

The invention also provides methods of protecting an object or a subject from radiation and/or from electronic pulses, where the methods comprise providing a material comprising melanin nanoshells between the object or subject to be protected and a source of the radiation and/or electronic pulses.

The invention further provides methods of protecting internal organs of a subject from radiation and/or from electronic pulses, where the methods comprise administering to the subject particles comprising melanin nanoshells.

The invention further provides methods of making a material comprising melanin nanoshells, where the method comprises fabricating melanin nanoshells into and/or onto the material; and materials comprising melanin nanoshells fabricated in and/or on the material.

BRIEF DESCRIPTION OF THE FIGURES

FIG. 16A-16F. Histology of GI track tissues obtained from CD-1 mice irradiated with 9 Gy at 3 Gy/min 4 hr (A-C) and 24 hr (D-F) post-irradiation: A) stomach, synthetic melanin group; B) stomach, ghosts melanin group; C) stomach, water; D) colon, synthetic melanin group; E) colon, ghosts melanin group; F) colon, water control group.

DETAILED DESCRIPTION OF THE INVENTION

Figure 1A:
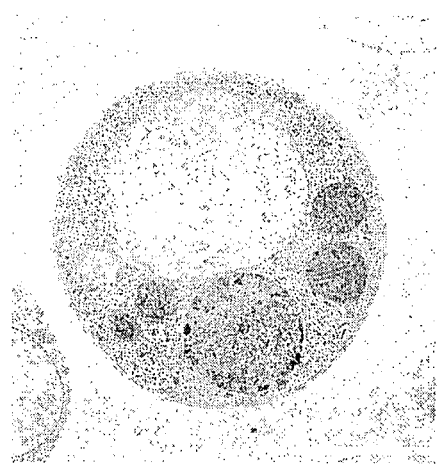
FIG. 1A-1C. Microscopic images of C. neoformans (Cn) cells. A) a transmission electron microscopy (TEM) image of non-melanized Cn cells; B) TEM image of melanized Cn cells; C) light microscopy image of melanin nanosize spheres. Melanized Cn cells were grown in Sabouraud dextrose broth medium with 1 mM 3,4-dihydroxyphenylalanin (L-dopa) for 5 days. Melanin spheres were generated by boiling melanized Cn cells in 6 M HCl.

The subject invention is directed to a nanoshell comprising melanin. Melanins are high-molecular weight pigments, arising in the course of oxidation and polymerization of phenols. The nanoshell can comprise polymerized L-dopa, epinephrine, methyldopa, a substituted phenol derivative and/or a phenolic derivative that polymerizes into melanin.

The nanoshell can comprise synthetic melanin and/or melanin isolated or derived from a biological source, such as a plant, an animal, a microorganism, and/or a melanin-containing cell, or generated by chemical synthetic process. Suitable animals include, but are not limited to, helminthes, cuttlefish and squids. The microorganism can be, e.g., a bacterium or preferably a fungus. Suitable fungi include, but are not limited to, *Cryptococcus neoformans* and/or *Histoplasma capsulatum*.

The melanin can comprise allomelanin, pheomelanin and/or eumelanin. Eumelanins are derived from the precursor tyrosine. Pheomelanin is derived from the precursors tyrosine and cysteine. Allomelanins are formed from nitrogen-free precursors such as catechol and 1,8-dihydroxynaphthalenes. In one embodiment, the nanoshell comprises pheomelanin and eumelanin, wherein the ratio of pheomelanin to eumelanin is at least 1:1. Preferably, the melanin contains divalent sulphur.

The nanoshell can comprises a nanosphere, a nanotube, a nanoellipsoid, a nanorod, a nanoball, or other suitable shape. The nanoshells can be hollow or filled with the same type of melanin as used in the shell or with a different type of melanin or with another material.

The nanoshell can have a thickness of about 10 nm to about 1,000 nm. In one embodiment, the nanoshell has a thickness of about 100 nm.

Preferably, the nanoshell has a linear attenuation coefficient for radiation that is at least 100-fold higher than that provided by powdered melanin that is not formed as a nanoparticle. More preferably, the nanoshell has a linear attenuation coefficient for radiation that is at least 1,000-fold higher than that provided by powdered melanin that is not formed as a nanoparticle. Most preferably, the nanoshell has a linear attenuation coefficient for radiation that is at least 10,000-fold higher than that provided by powdered melanin that is not formed as a nanoparticle.

Preferably, the nanoshell has a linear attenuation coefficient for radiation that is at least 10-fold higher than that provided by lead. More preferably, the nanoshell has a linear attenuation coefficient for radiation that is at least 100-fold higher than that provided by lead. Most preferably, the nanoshell has a linear attenuation coefficient for radiation that is at least 500-fold higher than that provided by lead.

The invention also provides a method of protecting an object or a subject from radiation and/or from electronic pulses, where the method comprises providing melanin nanoshells between the object or subject to be protected and a source of the radiation and/or electronic pulses. The melanin nanoshells can be fabricated in or on the source of the radiation and/or electronic pulses, and/or the melanin nanoshells can be fabricated in or on the object or subject to be protected from radiation and/or from electronic pulses.

As used herein, to protect against radiation and electronic pulses means to reduce the amount of radiation or electronic pulses reaching the object or subject to be protected, compared to the amount of radiation and electronic pulses that would reach the object or subject in the absence of the melanin nanoshells. The melanin can be internal and/or external to the object or subject. The radiation can comprise ionizing radiation. The radiation can be, for example, one or more of gamma radiation, x-ray radiation, solar radiation, cosmic radiation, electromagnetic radiation, bremsstrahlung radiation, ultraviolet radiation, and particulate radiation (e.g., α-radiation and β-radiation). The source of the radiation can be a medical isotope.

The melanin nanoshells can be, for example fabricated in a material, mixed in a material, layered in a material, or coated onto a material.

The object that is protected can be, for example, a computer, an electronic component or circuit, a printed circuit board, a cell phone, an avionic system and/or a satellite component. The subject that is protected can be an animal, a human, and/or a plant. For a human or animal subject, one or more internal organs can be protected, for example bone marrow, liver, spleen, kidneys, lungs, and/or portions or all of the gastrointestinal tract.

The melanin nanoshells can also be used to contain radiation and/or electronic pulses.

The invention further provides a method of protecting internal organs of a subject from radiation and/or from electronic pulses, where the method comprises administering to the subject particles comprising any of the melanin nanoshells described herein. The subject can be a human or an animal. The organ that is protected can be, for example, one or more of bone marrow, liver, spleen, kidneys, lungs, and gastrointestinal tract, e.g. the intestines. Preferably, bone marrow is protected. The method can further comprise administering to the subject a co-polymer of the poloxamer series, which can increase bone marrow uptake of the melanin particles. Preferably, the co-polymer of the poloxamer series is administered to the subject prior to administering the particles comprising the melanin nanoshell. Co-polymers of the poloxamer series include, for example, pluronic acid F-68, poloxamer-407 (PEG (polyethylene glycol)/PEO (polyethylene oxide), MW 13,310) (24), and poloxamine 908 (25, 28). The class of polyoxypropylene/polyoxyethylene copolymer nonionic surfactant compounds is reviewed in (27). Preferably, the particles comprising the melanin nanoshell have a diameter of about 10 nm to about 1,000 nm. The particles may be silica particles. Preferably, systemic administration such as e.g. intravenous administration is used to administer the melanin nanoshell particles and the poloxamer series co-polymer to the subject.

The invention further provides a method of making a material comprising the any of the melanin nanoshells disclosed herein, where the method comprises fabricating melanin nanoshells into and/or onto the material. The method can comprise polymerizing melanin or melanin nanoparticles onto a surface. The method can further comprise growing melanized fungi and extracting melanin nanoshells from the fungi. The fungi can be encapsulated in melanin nanospheres. The fungi can include, but are not limited to, *Cryptococcus neoformans* (Cn) and/or *Histoplasma capsulatum* (Hc). The fungi can be grown in the presence of a melanin precursor, where the melanin precursor is one or more of L-dopa (3,4-dihydroxyphenylalanin), D-dopa, catechol, 5-hydroxyindole, tyramine, dopamine, tyrosine, cysteine, m-aminophenol, o-aminophenol, p-aminophenol, 4-aminocatechol, 2-hydroxyl-1,4-naphthaquinone, 4-metholcatechol, 3,4-dihydroxynaphthalene, gallic acid, resorcinol, 2-chloroaniline, p-chloroanisole, 2-amino-p-cresol, 4,5-dihydroxynaphthalene, 1,8-dihydroxynaphthalene, 2,7-disulfonic acid, o-cresol, m-cresol, and p-cresol.

The invention also provides materials comprising melanin nanoshells fabricated in and/or on the material.

Since melanin nanoshells are negatively charged, they can be attracted or held in place with positively charged substances, or repelled using negatively charged substances.

The material, for example, can be coated with melanin nanoshells and/or encased in melanin nanoshells. The melanin nanoshells can be incorporated into the material. The material can be a plastic that is impregnated with melanin nanoshells or a surface where melanin is polymerized and/or melanin nanoshells are attached. The melanin nanoshells can be in a binder between two layers of material.

The material comprising the melanin nanoshells can be used, for example, as clothing, a protective gear, a object worn by a subject, or a packaging material. The material can be, or can be incorporated into, a wall, floor and/or ceiling of a room, building, vehicle, aircraft, ship, spacecraft, and/or submarine.

EXPERIMENTAL DETAILS

Materials and Methods

*C. neoformans* (Cn) and *H. capsulatum* (Hc). American Type Culture Collection (ATCC, Rockville, Md.) strains Cn 24067 (serotype D) and Hc (CIB strain 1980, a gift from A. Restrepo, Medellin, Colombia) were used in all experiments. Cn was grown in Sabouraud dextrose broth (Difco laboratories, Detroit, Mich.) for 24 hrs at 30° C. with constant shaking at 150 rpm. Hc was grown with shaking at 37° C. in defined media consisting of 29.4 mM $KH_2PO_4$, 10 mM $MgSO_4 \times 7H_2O$, 13 mM glycine, 15 mM D-glucose, 3 μM thiamine. Melanized Cn and Hc cells were generated by growing the fungi in their respective media with 1 mM 3,4-dihydroxyphenylalanin (L-dopa) for 5 days. The cells were collected by centrifugation and washed three times with PBS, pH 7.2 before radiation exposure.

Susceptibility of Cn and Hc to external gamma radiation. Approximately $10^5$ melanized or non-melanized Cn or Hc cells were placed in microcentrifuge tubes in 0.5 mL PBS and irradiated with a $^{137}Cs$ source at a dose rate of 14 Gy/min. The cells were exposed to doses of up to 220 Gy. The exposures of 1,000-8,000 Gy were given by irradiating the cells at 30 Gy/min. Following radiation exposure, $10^3$ cells from each tube were plated to determine viability as measured by colony forming units (CFU's). Alternatively, melanized or non-melanized Cn cells were plated on Sabouraud plates in air or under the nitrogen gas. The plates were irradiated at a dose rate of 14 Gy/min followed by determination of viability as measured by CFU's.

Other sources of melanin. Melanin from cuttlefish *Sepia officinalis* was purchased from Sigma Chemical Co.

Measurement of radiation absorption properties of bulk melanin. A pellet of 13 mm diameter and 4 mm height with the mass of 0.71 g and density of 1.33 $g/cm^3$ was made from *Sepia* melanin by applying a pressure of 6 $tonn/cm^2$. The measuring of gamma radiation shielding properties of the pellet was performed by placing the pellet on the 3 mm in diameter opening in a lead-shielded castle inside which radioactive sources were placed. The dose rate in mrad/h at the surface of the opening was measured with and without the melanin pellet. Absorption of α- and β-radiation was evaluated by placing the melanin pellet on the point sources of 210-Polonium and 32-Phosphorus, respectively.

Transmission electron microscopy (TEM). Melanized and non-melanized Cn and Hc were frozen under high pressure using a Leica EMpact High Pressure Freezer (Leica Microsystems, Austria). Frozen samples were transferred to a Leica EM AFS Freeze Substitution Unit and freeze substituted in 1% osmium tetroxide in acetone. They were brought from −90° C. to room temperature over 2-3 days, rinsed in acetone and embedded in Spurrs epoxy resin (Polysciences, Warrington, Pa.). Ultrathin sections of 70-80 nm were cut on a Reichert Ultracut UCT, stained with uranyl acetate followed by lead citrate and viewed on a JEOL (Tokyo, Japan) 1200EX transmission electron microscope at 80 kV.

Isolation and purification of melanins. The cells were suspended in 1.0 M sorbitol-0.1 M sodium citrate (pH 5.5). Lysing enzymes (Sigma Chemical Co.) were added to suspension at 10 mg/mL and the suspensions were incubated overnight at 30° C. Protoplasts were collected by centrifugation and incubated in 4.0 M guanidine thiocyanate overnight at room temperature and were frequently vortexed. The resulting particulate material was collected by centrifugation, and the reaction buffer (10.0 mM tris, 1.0 mM $CaCl_2$, 0.5% SDS) was added to the particles. Proteinase K was added to suspension at 1.0 mg/mL followed by overnight incubation at 37 (Hc) or 65° C. (Cn). The particles were boiled in 6.0 M HCl for 1 hour. Finally, resulting material was washed with PBS, dialyzed against deionized water overnight and dried in the air at 65° C. for 2 days. Approximately $1.5 \times 10^{10}$ Cn cells and $2.2 \times 10^{10}$ Hc cells were used. The isolation procedure yielded approximately 2.0 mg melanin per $10^{10}$ cells for Cn, and 2.3 mg per $10^{10}$ cells for Hc. The yield of melanized cells per 1 liter of medium is 2 g and the yield of purified ghosts is 0.3 g. Hollow melanin shells that remain after the treatment of melanized cells with enzymes, guanidinium isothiocyanate and 6 M HCl were dubbed "ghosts" because they preserved the shape of the cells.

Quantitative elemental analysis of melanins. Elemental analysis for carbon, hydrogen, and nitrogen was performed by Quantitative Technologies Inc. (Whitehouse, N.J.).

Oxidation of melanins and HPLC of oxidized melanins. Cn and Hc melanin underwent acidic permanganate oxidation using the procedure described by Ito and Fujita (16). Pyrrole-2,3,5-tricarboxylic acid (PTCA) and 1,3-thiazole-4,5-dicarboxylic acid (TDCA) were used as standard compounds. The oxidation products were analyzed by HPLC using a Shimadzu LC-600 liquid chromatograph, Hamilton PRP-1 $C_{18}$ column (250×4.1 mm dimensions, 7 μm particle size), and Shimadzu SPD-6AV UV detector. The mobile phase was 0.1% trifluoroacetic acid in water (solvent A) and 0.1% trifluoroacetic acid in acetonitrile (solvent B). At 1.0 mL/min, the elution gradient was (min, % B): 0, 0; 1, 0; 12, 25; 14, 25; 16, 0. The UV detector was set at a 255 nm absorbance.

MALDI mass spectrometry. The major peaks generated during chromatography of oxidized melanins were collected and analyzed by MALDI-TOF mass spectrometry in positive pressure mode on PE-Biosystems Mariner ESI TOF mass spectrometer. Peptide mixture with molecular weights of 1059.56, 1296.68 and 1672.95 in 2,5-dihydroxybenzoic acid matrix was used for calibration.

Electron spin resonance spectroscopy (ESR). The ESR of purified melanins from Cn and Hc cells was performed on ER 200D EPR/ENDOR spectrometer with ESP 300 upgrade (Brucker Instruments, Inc. Billerica, Mass.).

Statistical analysis. The slopes of the survival curves were determined by linear regression (GraphPad PRISM software, San Diego, Calif.) and a Student's test for unpaired data was performed to analyze the differences in survival. Differences were considered statistically significant when P values were <0.05.

Results and Discussion

Figure 1B:
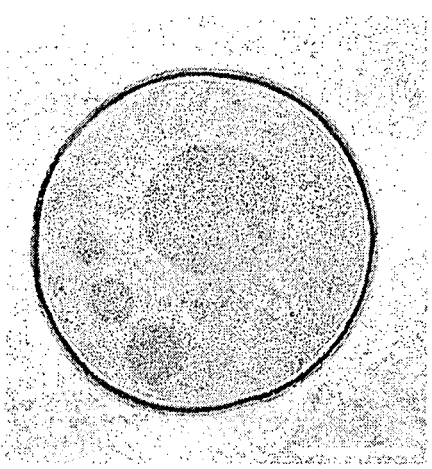
Figure 1C:
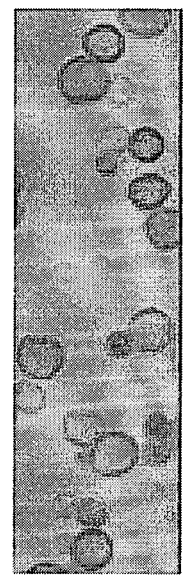

As described herein, the ability of melanin to protect against ionizing radiation was demonstrated in two fungi capable of melanogenesis, *Cryptococcus neoformans* (Cn) and *Histoplasma capsulatum* (Hc). These fungi were chosen as model organisms because they can be grown in either melanized or non-melanized states, while fungi found in Chernobyl are constitutively melanized. Cn and Hc cells became encapsulated in melanin when grown with L-dopa (3,4-dihydroxyphenylalanin). Previous work (2) as well as this study showed that all melanin in the cells is concentrated in the cell wall (FIG. 1B). The melanin forms coherent and robust spheres capable of withstanding boiling in concentrated hydrochloric acid (FIG. 1C). From transmission electron microscopy (TEM) of melanized Cn and Hc, the thickness of the melanin layer was estimated to be 100 nm. Analysis of 'ghost' particles recovered from *C. neoformans* grown with different precursors reveals that the pigments and melanins made from different precursors have different properties with regards to color, charge, and electron spin resonance.

Figure 2A:
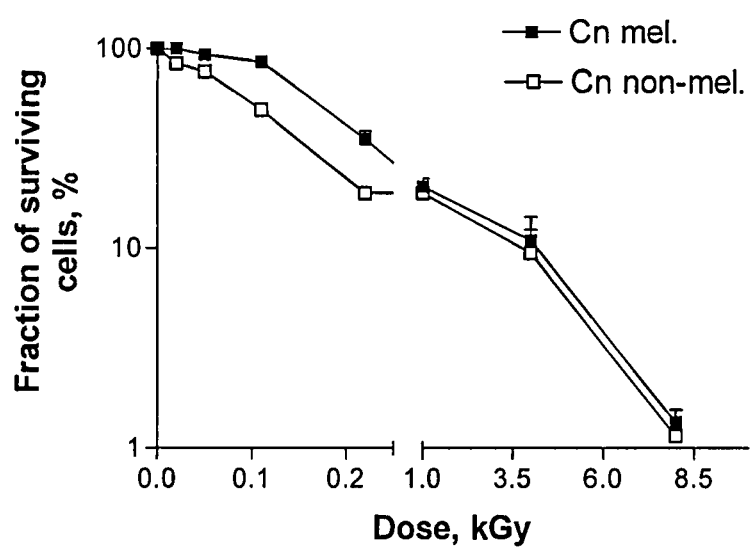
FIG. 2A-2D. Survival of non-melanized and melanized Cn and H. capsulatum (Hc) cells following exposure to external gamma rays: A) Cn in PBS up to 220 Gy at 14 Gy/min and up to 8,000 Gy at 30 Gy/min; B) Hc in PBS up to 220 Gy at 14 Gy/min and up to 8,000 Gy at 30 Gy/min; C) melanized and non-melanized Cn on Sabouraud plates irradiated at 14 Gy/min up to 440 Gy in air; D) in $N_2$.
Figure 2B:
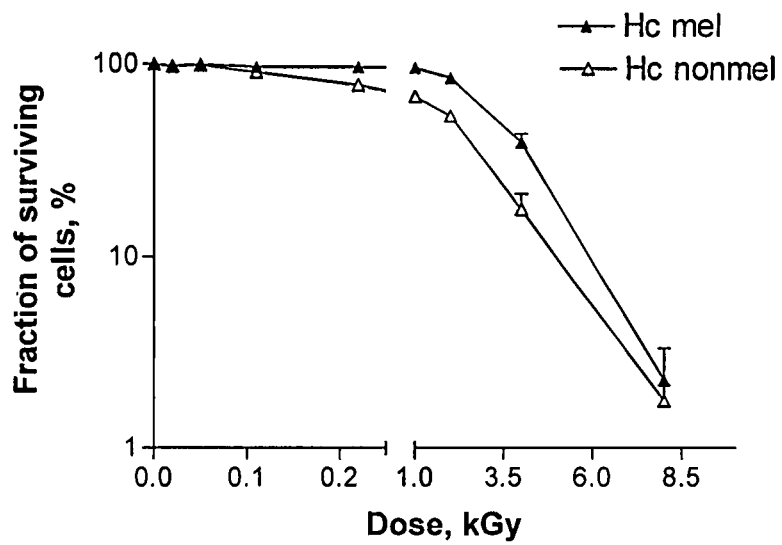
Figure 2C:
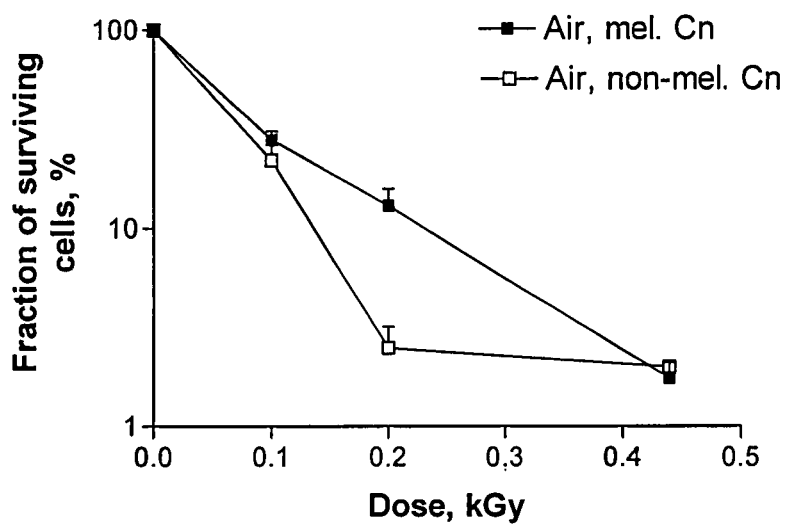
Figure 2D:
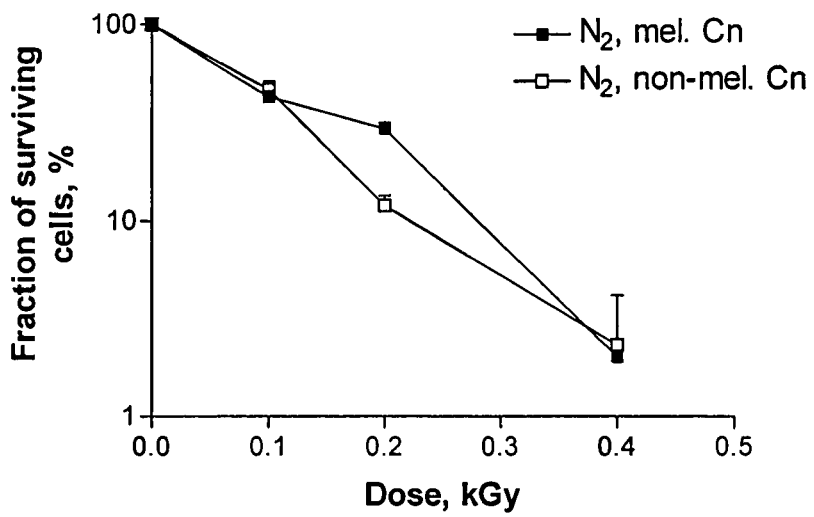

Melanized and non-melanized Cn and Hc cells in phosphate buffered saline (PBS) were subjected to extremely high doses of radiation—up to 8,000 Gy. For comparison, a dose of just 5 Gy is lethal to humans. The radioprotective effect of melanin was more readily demonstrable at the higher radiation doses, as the $LD_{90}$ for these organisms in non-melanized form is around 50 Gy (Cn) or 100 (Hc) Gy (11). Melanized Cn cells demonstrated reduced susceptibility to external gamma radiation (P=0.01) in the dose range of 0-220 Gy (FIG. 2A). At the dose range of 1,000-8,000 Gy some protective effects were also seen for melanized Cn cells (FIG. 2A); however, the difference in survival of irradiated cells was not statistically significant (P=0.4). For Hc cells melanin provided protection against gamma radiation up to 8,000 Gy (P<0.01) (FIG. 2B). Since some of the cytocidal effects of radiation are mediated by radiolysis of water and are significantly more pronounced in the presence of $O_2$ (12), the effects of radiation on Cn cells were compared in air and in $N_2$ atmospheres. When Cn cells were irradiated directly on agar plates either in air (FIG. 2C) or in $N_2$ (FIG. 2D) with the doses of up to 440 Gy, less killing was observed in $N_2$ than in air (P<0.02) for both melanized and non-melanized Cn cells in the 150-300 Gy region. In both air and $N_2$, melanization conferred a greater survival advantage for Cn (P<0.01).

To compare the radioprotective properties of melanin with other materials such as lead, the linear attenuation coefficient and half value layer were calculated according to the equations:

$$I = I_o e^{-\mu x} \quad (1)$$

$$HVL = 0.693/\mu \quad (2)$$

where $I_o$ and $I$ are the radiation intensity before and after shielding, respectively; $\mu$ is the linear attenuation coefficient in $cm^{-1}$, x is the thickness of the shield in cm, and half value layer (HVL) is the thickness of shielding necessary to reduce the intensity of radiation to half of its original value. The reduction in radiation intensity was calculated from the linear parts of survival curves assuming that a 10% increase in survival is equivalent to a 10% decrease in radiation intensity. Linear attenuation coefficient and HVL for Hc melanin were calculated to be $1.4 \times 10^4$ $cm^{-1}$ and 0.5 μm, respectively. This melanin linear attenuation coefficient is several orders of magnitude higher than that of lead (27.1 $cm^{-1}$) (13), indicating that fungal melanin in nanosphere form is a much more efficient radioprotector than lead.

Figures 3A, 3B:
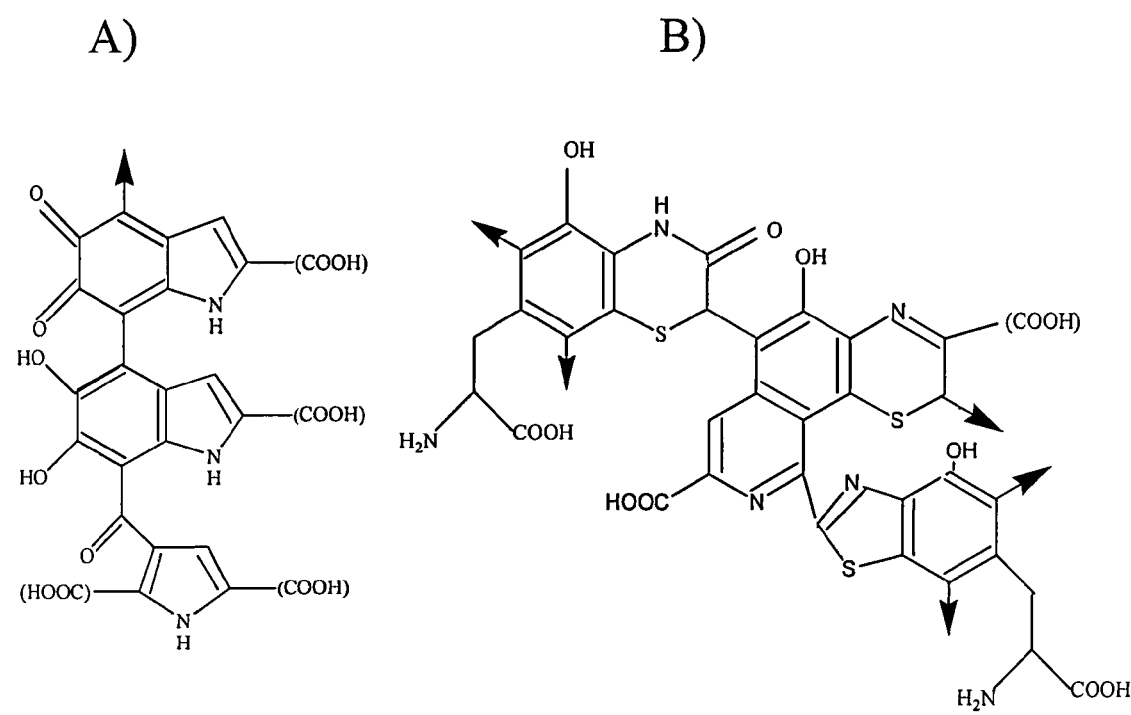
FIG. 3A-3F. High-pressure liquid chromatography (HPLC) of permanganate-oxidized melanins: A) structure of eumelanin oligomer; B) structure of pheomelanin oligomer (adapted from ref. 17); C) visual appearance of oxidized melanin samples, from left to right: Cn, Hc; D) chromatogram of background solution; E) Cn melanin; F) Hc melanin.
Figure 3C:
Figure 3D:
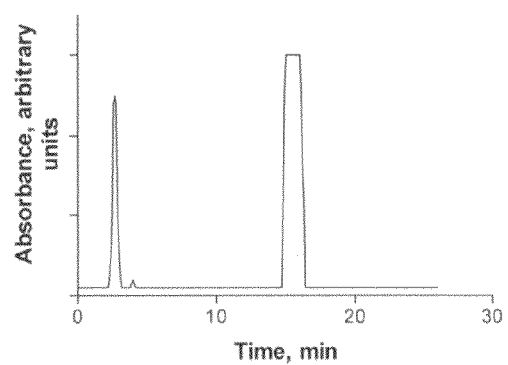
Figure 3E:
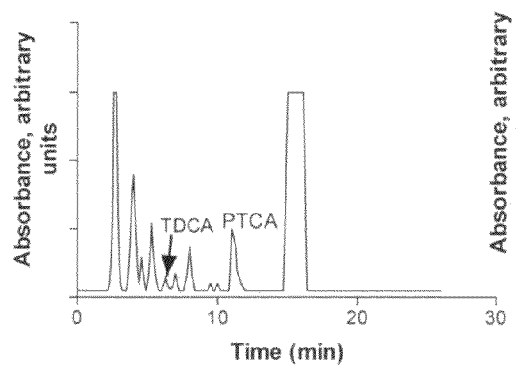
Figure 3F:
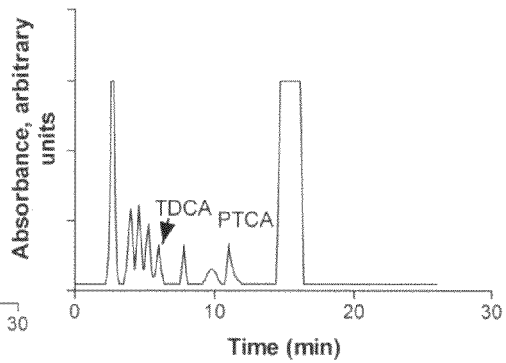

To gain insights into the unusual radioprotective properties of melanin, high-pressure liquid chromatography (HPLC), matrix assisted laser desorption/ionization time of flight mass spectrometry (MALDI-TOF) and elemental analysis of the fungal melanins were performed. Unlike synthetic melanins (10, 14, 15), the structures of natural melanins including fungal melanin are poorly understood. These pigments are amorphous and insoluble, characteristics that preclude a structural solution of melanins given currently available analytical tools, and have to be converted into low molecular weight fragments prior to analysis. Consequently, acidic permanganate oxidation of fungal melanins was carried out before HPLC. Two major types of melanin have been described. Eumelanin is a dark-brown to black pigment with 6-9% nitrogen and 0-1% sulphur, and is composed of 5,6-dihydroxyindole (DHI) and 5,6-dihydroxyindole-2-carboxylic acid (DHICA) monomer units (16, 17) (FIG. 3A). In contrast, pheomelanin is a reddish-brown pigment with 8-11% nitrogen and 9-12% sulfur, composed of benzothiazine monomer units (16, 17) (FIG. 3B). Acidic permanganate oxidation yields pyrrole-2,3,5-tricarboxylic acid (PTCA) from DHICA-derived structures, and 1,3-thiazole-4,5-dicarboxylic acid (TDCA) from benzothiazole subunits (16, 17). Hence, the presence of PTCA in oxidation products indicates eumelanin and the presence of TDCA indicates pheomelanin. The appearance of solutions following acidic permanganate oxidation of melanins is shown in FIG. 3C. Chromatograms of PTCA and TDCA standards yielded peaks at 11 and 6.1 min, respectively. The chromatograms of both Cn and Hc melanins revealed PTCA and TDCA (FIG. 3E, 3F). The MALDI-TOF analysis of these peaks confirmed the presence of PTCA (MW 199) and TDCA (MW 173). Importantly, the PTCA to TDCA ratio was 0.90 for Hc melanin, whereas for Cn melanin the ratio was 47.7, as calculated from the chromatographic data. Although these ratios do not reflect quantitative measure of eumelanic/pheomelanic character, they indicate that benzothiazine subunits predominate in Hc melanin while DHICA subunits predominate in Cn melanin. The low TDCA content in Cn is consistent with very low levels of aminohydroxyphenylalanine in Cn, which is a specific indicator of cysteinyldopa (18). In contrast, the relatively high levels of TDCA in Hc melanin suggest a significant higher content of pheomelanin. This observation is also consistent with the fact that Hc colonies often display some measure of pigmentation, and red Hc colonies have been described (19). The results of elemental analyses of various melanins performed in this study as well as reported in the literature (20) are given in Table 1. The C:N ratio for Cn melanin was 11.4:1, while that for Hc melanin was significantly higher—18.6:1 (20).

TABLE 1

Elemental composition of various melanins

| Type of Melanin | C/N Ratio | Reference |
|---|---|---|
| l-dopa-melanin | 6.65 | 16 |
| Copolymer of l-dopa and of 5-S-Cysteinyl-dopamine | 6.75 | 16 |
| 5-S-Cysteinyldopa-melanin | 5.02 | 16 |
| Pheomelanin from l-dopa and cysteine | 4.95 | 16 |
| Dopamine-melanin | 7.02 | 16 |
| 5-S-Cysteinyldopamine-melanin | 4.41 | 16 |
| C. neoformans 24067 black particulate | 12.5 | 2 |
| Sigma melanin | 7.5 | 2 |
| Synthetic l-dopa-melanin | 9.0 | 20 |
| Dopa-melanin from S. officinalis | 7.0 | 20 |
| Dopa-melanin from C. neoformans 24067 | 8.0 | 20 |
| Melanin from A. niger J9901 conidia | 14.5 | 20 |
| Melanin from MNT1 melanoma tumor | 6.3 | 23 |
| Melanin from C. neoformans 24067 | 11.41 | This work |
| Melanin from H. capsulatum CIB 1980 | 18.63 | This work |

C = carbon;
N = nitrogen.

Since the density of melanin is only slightly greater than that of water, it cannot contribute significantly to its remarkable radioprotective properties. However, the number of electrons per gram could make a significant contribution to melanin protective properties. The number of electrons is an especially important contributor to the attenuation properties of a material at the energy levels where the Compton effect predominates (13). Thus, the higher number of electrons in oligomers of pheomelanin in comparison with eumelanin—388 versus 287, and the structure composed of electron-rich covalently linked aromatic motifs could account for better scattering properties of Hc melanin rich in pheomelanin oligomers in comparison with Cn. Secondly, pheomelanin contains divalent sulfur (FIG. 3B) which may also contribute to superior radioprotective properties of Hc melanin, as compounds containing divalent sulfur are efficient radioprotectors (12).

Figure 4:
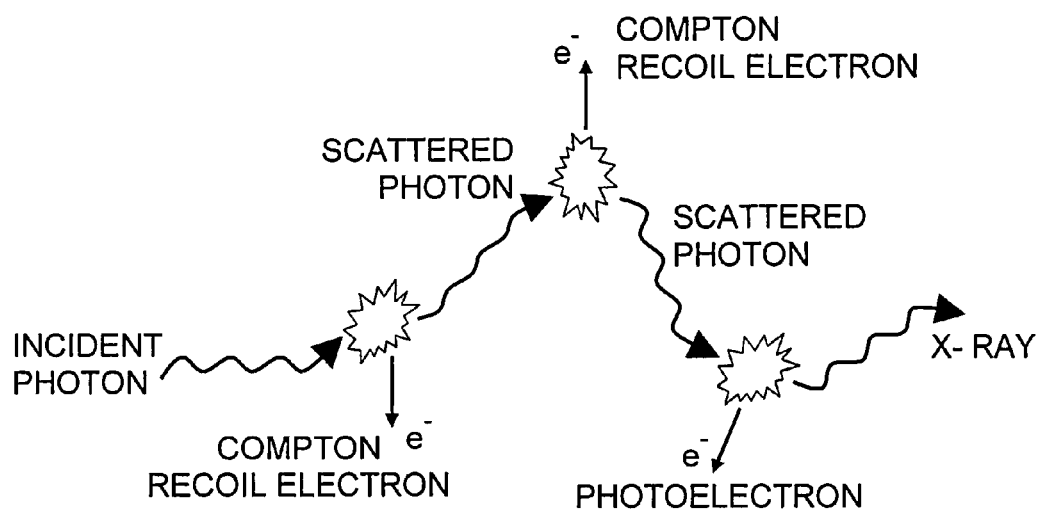
FIG. 4. Diagram illustrating multiple interactions of a photon passing through matter. Energy is transferred to electrons in a sequence of photon-energy degrading interactions (adapted from (22)).
Figure 5:
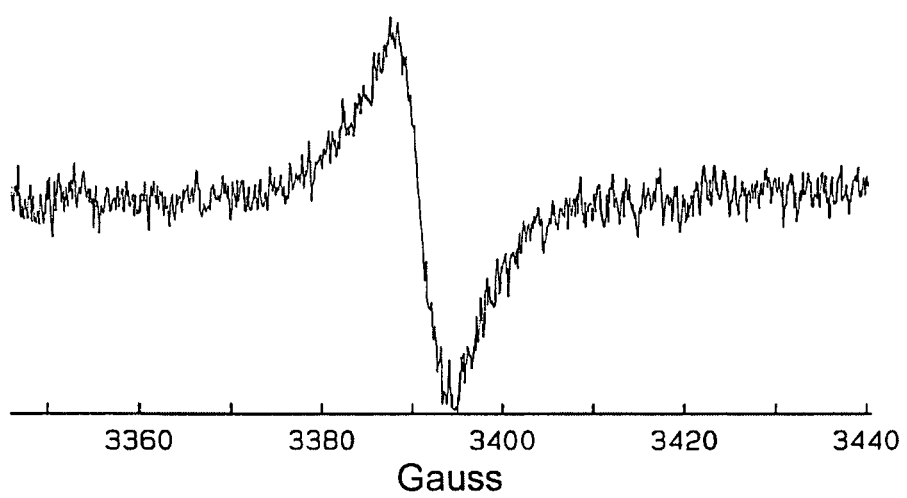
FIG. 5. Electron spin resonance spectroscopy (ESR) spectrum of melanized Hc cells showing characteristic spectrum of melanin.

Efficient Compton scattering by melanin alone is unlikely to explain the radioprotective properties of melanin. The transfer of radiation (photon) energy to living matter occurs in a series of interactions, where energy is transferred to high-energy electrons, and then to secondary photons of progressively less energy (FIG. 4). These high-energy electrons are ultimately responsible for the radiobiologic effects caused by gamma-ray, x-ray or bremsstrahlung radiation by either direct "hits" of DNA or through radiolysis of water in the cells which results in formation of reactive short-lived free radicals such as hydroxyl OH or perhydroxyl $HO_2$, both capable of damaging DNA. Hence, melanin may trap these high-energy electrons thus preventing them from entering a cell and triggering radiolysis of water. Consistent with this hypothesis, electron spin resonance spectroscopy (ESR) of fungal melanins revealed strong signals for melanized Hc (FIG. 5) and Cn (results not shown) indicative of a stable radical population (21). Thus, these stable free radicals may act as efficient traps of Compton and photoelectrons and short-lived free radicals.

In the macroscale experiment, the 4 mm thick melanin pellet made of Sepia (bulk) melanin completely absorbed α- and β-radiation from 210-Po and 32-P sources, respectively. This is better than plastic, since to stop a β-particle 7 mm of plastic (e.g., Lucite) are needed and the density of Lucite is higher than the density of the 1.33 g/cm$^3$ melanin pellet made of Sepia melanin.

Measurement of the bulk melanin shielding effect towards gamma radiation of 122-140 keV energies showed that 4 mm of melanin cut the dose by ~33%. Using these data, the linear attenuation coefficient (μ) for bulk melanin was calculated to be 1.01 cm$^{-1}$. For comparison, at 140 keV lead has a higher μ=27.1 cm$^{-1}$ but its density is 11.34 g/cm$^3$; and aluminum has μ=0.386 cm$^{-1}$ and a density of 2.7 g/cm$^3$. It is obvious from these measurements, that melanin nanoparticles possess several orders of magnitude better radiation shielding properties than bulk melanin. Since the absorbance of radiation by matter also depends on the geometric arrangement of the photon source and the absorber, an important factor contributing to the radioprotective properties of fungal melanin can be the spatial arrangement of melanin in fungal cells. The location of melanin in the fungal cell wall outside of the plasma membrane (FIG. 1) where it forms a sphere of nanosize thickness places it in a position such that incident radiation must unavoidably pass thorough the melanin layer which scatters and/or absorbs it.

Figures 6A, 6B:
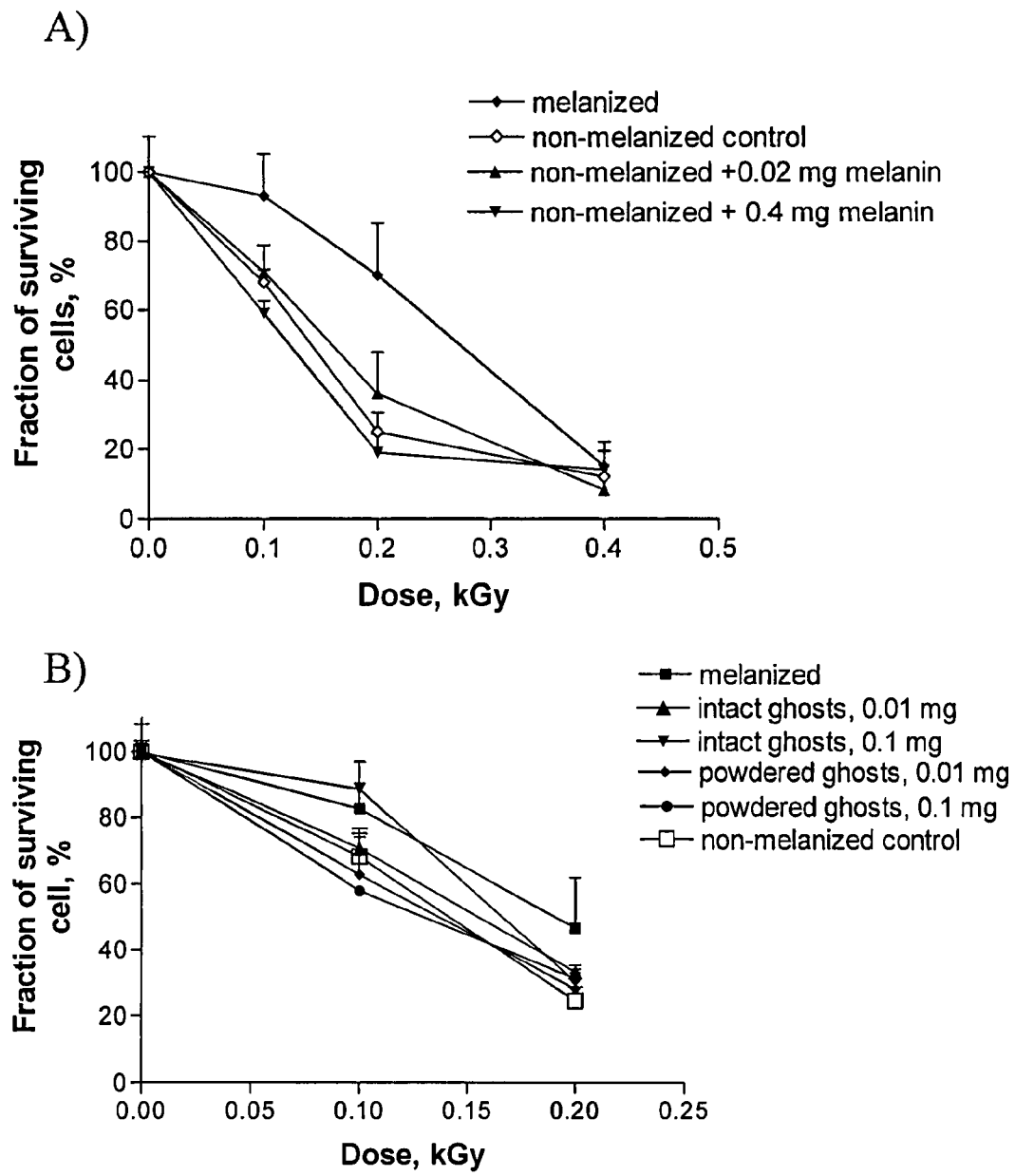
FIG. 6A-6B. Survival of non-melanized and melanized fungal cells following exposure to external gamma rays. A) melanized and non-melanized *C. neoformans* irradiated at 14 Gy/min up to 400 Gy, 0.02 or 0.4 mg of *S. officinalis* melanin was added to non-melanized cells. B) melanized and non-melanized *C. neoformans* irradiated at 14 Gy/min up to 200 Gy, 0.01 or 0.1 mg of intact or crushed *C. neoformans* melanin "ghosts" was added to samples. Cn—*C. neoformans*, Hc—*H. capsulatum*.

To prove the contribution of the nanospherical arrangement of melanin in fungal cells to radioprotection, non-melanized C. neoformans cells were irradiated with doses of up to 400 Gy in the presence of melanin from Sepia officinalis (cuttlefish), which is not arranged in hollow spheres, in amounts equal or 20 times higher than the amount of melanin in the same number of melanized C. neoformans cells. S. officinalis melanin conferred no protection at any dose (FIG. 6A), suggesting that the spatial arrangement of melanin particles in the 'ghosts' was important in radioprotection. To exclude the possibility that differences in chemical composition of fungal and S. officinalis melanins accounted for the lack of radioprotection by the latter, the experiment was modified by irradiating non-melanized C. neoformans cells with the same amounts of intact and powder-crushed melanin "ghosts" (FIG. 6B). 0.1 mg intact "ghosts" protected the cells up to 120 Gy in the same way as melanization, while crushed "ghosts" afforded only slight protection. Hence, when melanin is arranged in nanospheres, it scatters/absorbs radiation more efficiently than powdered melanin of the same chemical composition.

Figure 7:
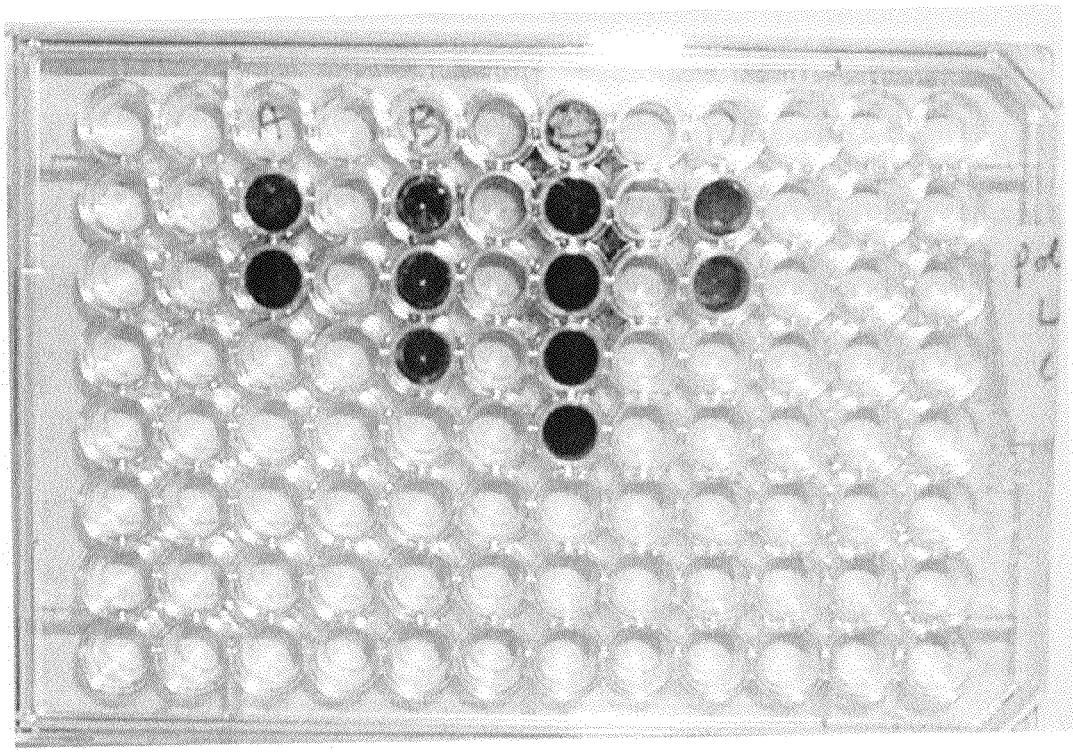
FIG. 7. Poly-lysine-precoated wells in a 96-well ELISA plate were filled with the suspensions of the following substances in poly-lysine solution: A—*Sepia* melanin; B—*C. neoformans* ghosts; C—charcoal. For control lead foil was used (D).
Figure 8:
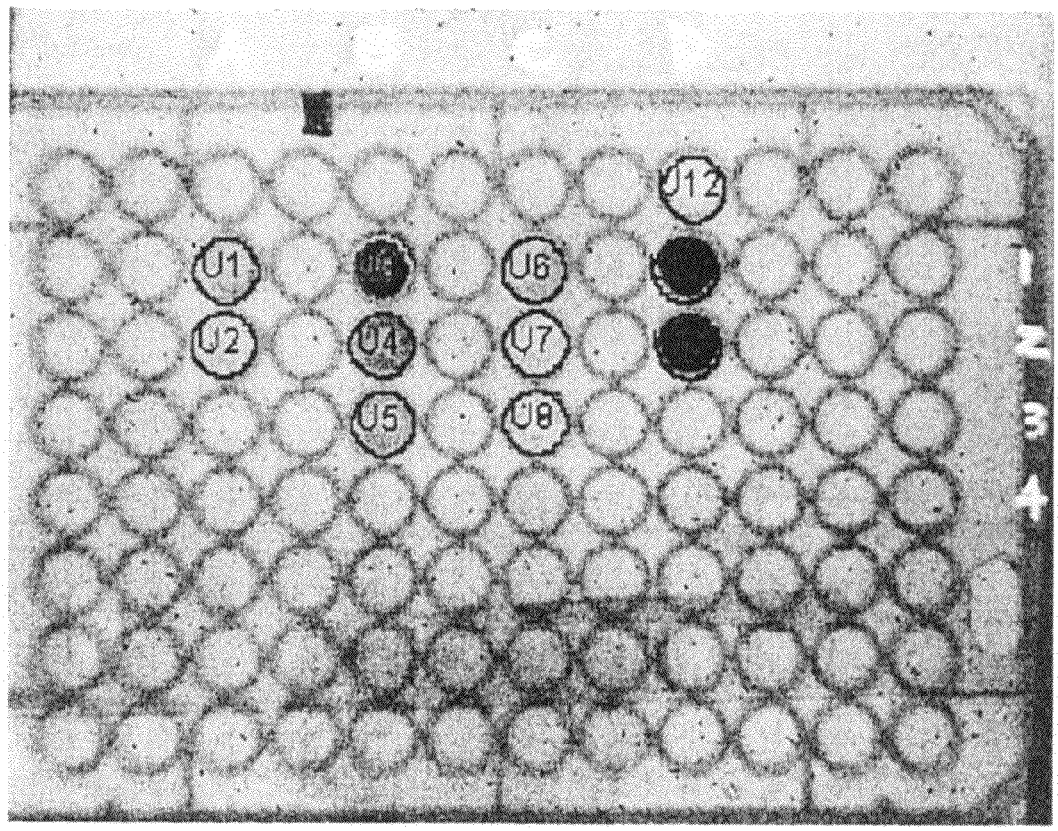
FIG. 8. The image of the radiographic film showing different exposures of the film depending on the substance in the wells. A—*Sepia* melanin; B—*C. neoformans* ghosts; C—charcoal. For control lead foil was used (D).

To further assess the shielding properties of *C. neoformans* melanin "ghosts", a 96 well ELISA plate was coated with a solution of poly-lysine to make the surface of the wells positively charged in order to counteract the negative charge carried by melanin "ghosts". The ghosts were mixed with poly-lysine solution to prepare a homogeneous suspension, and 3 different concentrations of ghosts were placed in the wells. For control different concentrations of *Sepia* melanin and charcoal suspensions in poly-lysine solution were used as well as lead foil of similar weights (FIG. 7). The ELISA plate was exposed to diagnostic X-rays (40 kVp at 10 mA) and the shielding effect was detected with Hi-speed Kodak x-omat (xb-1) radiographic film placed under the plate during exposure to X-rays (FIG. 8). The radiographic film was analyzed for corresponding global intensities by subtraction method (Biorad Quantity One software) and internal pixel density (IPD) per $mm^2$ was calculated. The attenuation of X-rays by substances in the wells was calculated as the ratio of IPD in the wells to IPD of the background wells (Table 2).

TABLE 2

Attenuation of diagnostic X-ray by suspensions of *C. neoformans* and Sepia melanin in comparison with non-melanin substances.

| | Amount, mg | Internal pixel density (IPD) per $mm^2$ 1st | 2nd (repeat) | mean IPD/ IPD (bkrd) | Attenuation (%) |
|---|---|---|---|---|---|
| A Sepia melanin | 50 | 1370 | 1370 | 1.12 | 12 |
| | 25 | 1280 | 1280 | 1.05 | 5 |
| B *C. neoformans* | 100 | 1720 | 1720 | 1.41 | 41 |
| | 50 | 1470 | 1470 | 1.21 | 21 |
| | 30 | 1346 | 1346 | 1.11 | 11 |
| C Charcoal | 40 | 1329 | 1329 | 1.09 | 9 |
| | 20 | 1248 | 1248 | 1.02 | 2 |
| | 15 | 1244 | 1244 | 1.02 | 2 |
| D Lead foil | 100 | 2202 | 2217 | 1.81 | 81 |
| | 200 | 2269 | 2277 | 1.87 | 87 |
| Background | — | 1218 | 1218 | 1 | 0 |

These results demonstrate that *C. neoformans* ghosts possess superior radiation shielding properties in comparison with other types of melanin (*Sepia*) or non-melanin carbon-based compounds (charcoal). The shielding properties of the ghosts were comparable to those of lead when one takes into consideration that the ghosts were used in the form of a suspension in poly-lysine solution, which has a lot of "gaps" between the ghosts for X-rays to penetrate without being scattered, while lead foil is a material with continuous close packing of lead atoms.

The properties of materials change dramatically when one moves from bulk materials to nanomaterials. The superior radiation shielding properties of fungal melanin nanospheres in comparison with melanin powder (bulk material) are direct consequence of principally different mechanism of radiation absorption by melanin nanoparticles—a gamma photon becomes "trapped" within a melanin nanoparticle as it is reflected several times by its inner walls and is unable to escape the particle until it transfers all of its energy to melanin.

Melanized Nanoparticles for Protection of Bone Marrow and Internal Organs from Ionizing Radiation As bone marrow is the dose-limiting organ for both external beam radiation therapy and radioimmunotherapy, protection of bone marrow against radiation would increase safety and efficacy of these treatments. An investigation was conducted of whether melanin nanoshells administered before a dose of external radiation protect bone marrow in mice from radiation damage. It is known that, following intravenous administration of nanoparticles, 0.5-1% of the injected dose goes into bone marrow, while the majority of nanomaterial is sequestered by the mononuclear phagocytes of the liver and to a lesser degree of the spleen (24). It has been demonstrated that nanoparticles can be efficiently redirected into the bone marrow in rats by pre-treatment or co-administration of block co-polymers of the poloxamer series, for example, poloxamer-407 (PEG (polyethylene glycol)/PEO (polyethylene oxide), MW 13,310) (25), which minimizes interaction of nanoparticles with the reticuloendothelial elements of liver and spleen.

Silica nanoparticles (20 nm) were utilized in the present experiments. The surface of unmodified silica particles is covered with hydroxyl groups. Nanoparticles were melanized overnight at 35° C. in 10 nM L-Dopa solution, precipitated by lowering the pH to 1, washed from unreacted L-Dopa and transferred into deionized water. To prove that the dark color of melanized particles was due to the presence of melanin, immunofluorescence of these particles was performed with melanin-binding monoclonal antibody (mAb) 6D2 as previously described (26). 6D2 mAb bound avidly to the surface of the particles, thus proving that they were covered with a layer of melanin.

Figure 9A:
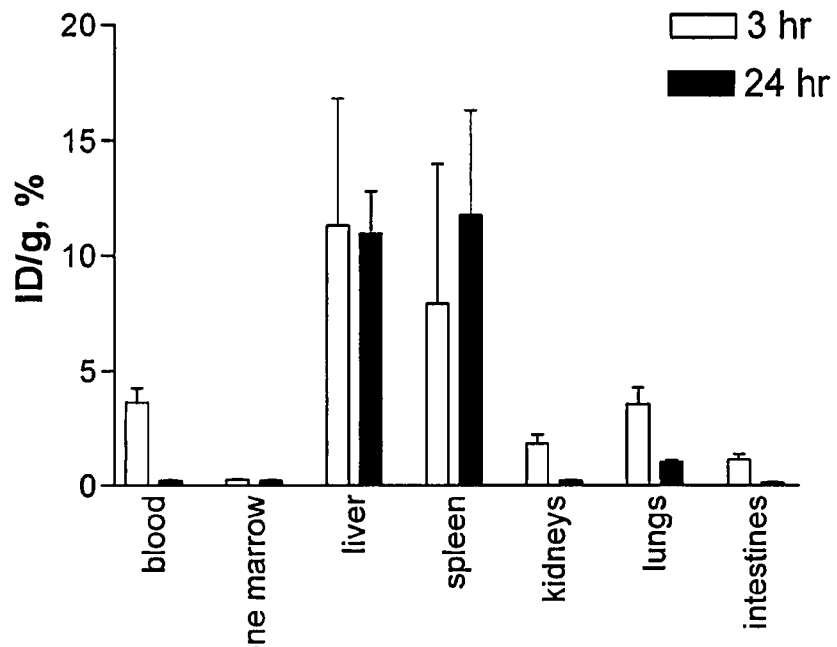
FIG. 9A-9B. Biodistribution of $^{188}$Re-labeled melanized 20 nm silica nanoparticles in BALB/c mice. A) Biodistribution following administration of nanoshell particles only. B) Biodistribution following pre-treatment with pluronic acid followed by administration of nanoparticles. Mice were injected IV with melanized particles. Pluronic acid (0.13 mg/kg body weight) was injected IV 3 hours earlier.
Figure 9B:
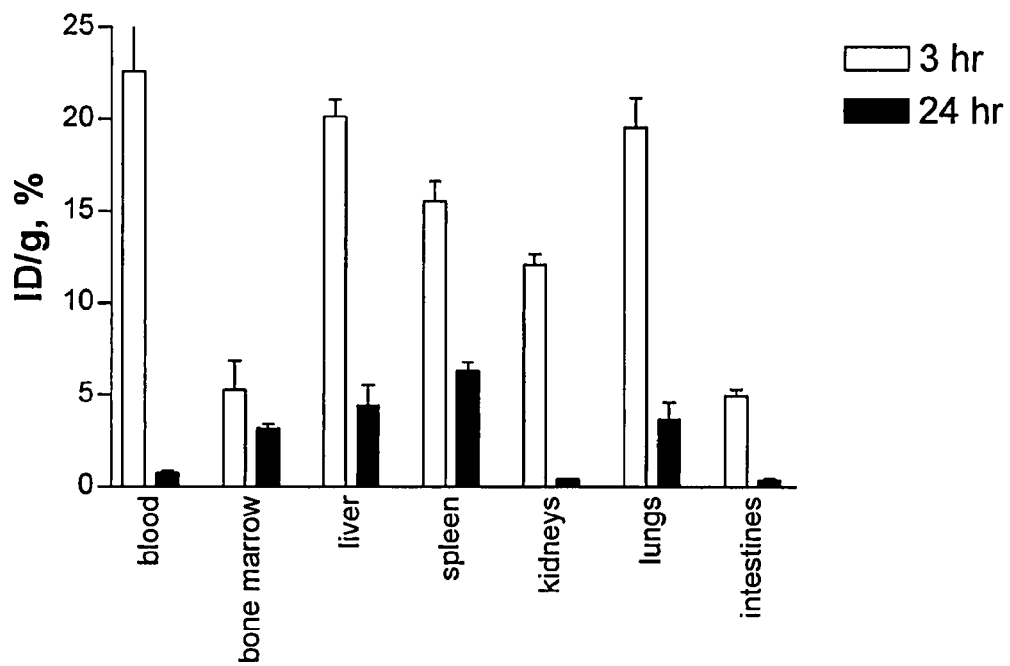
Figure 10A:
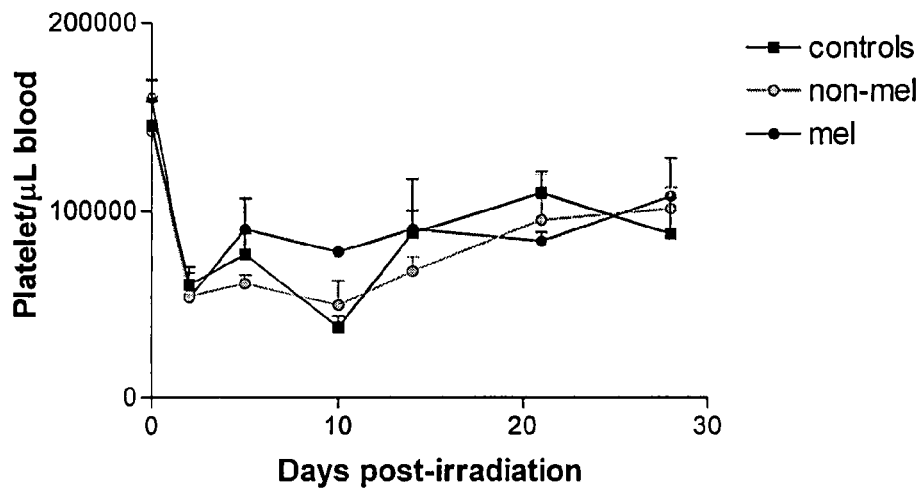
FIG. 10A-10D. Platelet (A, B) and white blood cell (WBC) (C, D) counts in mice pre-treated with melanized nanoparticles and irradiated with 1.25 Gy of gamma radiation.
Figure 10B:
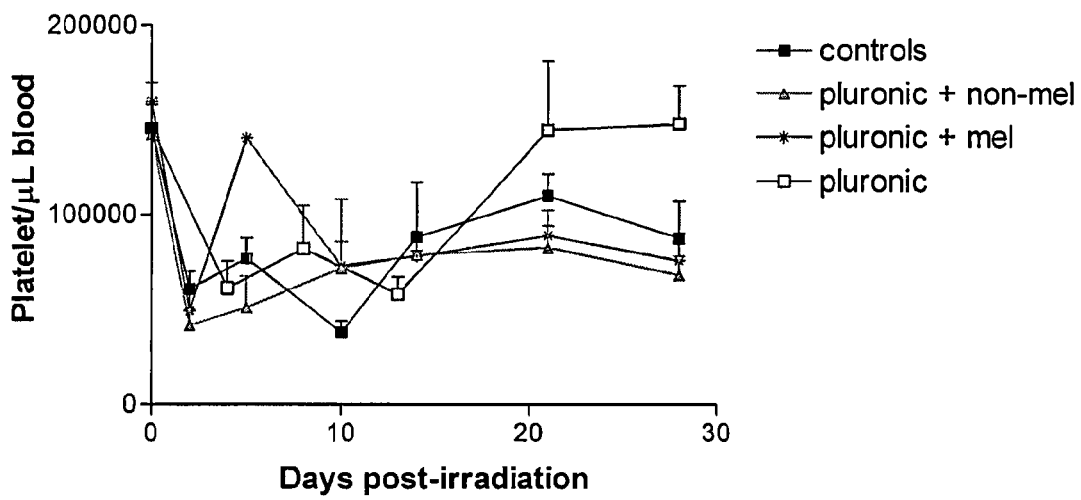
Figure 10C:
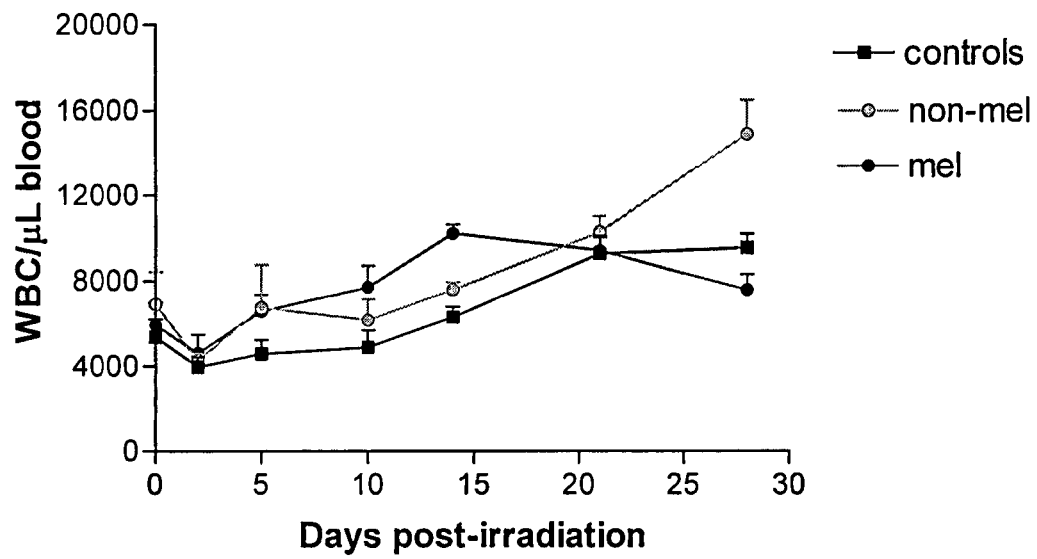
Figure 10D:
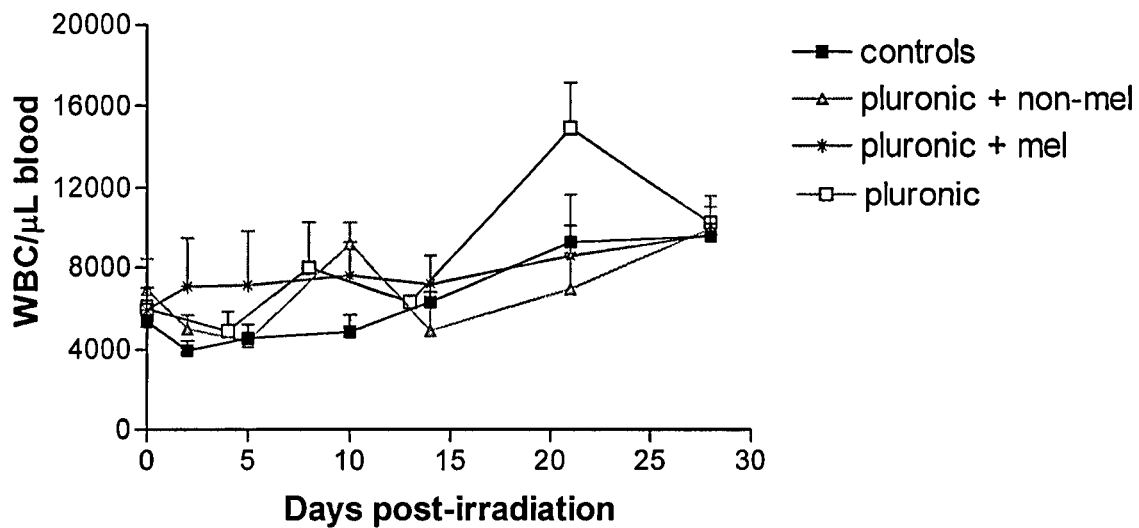
Figure 11A:
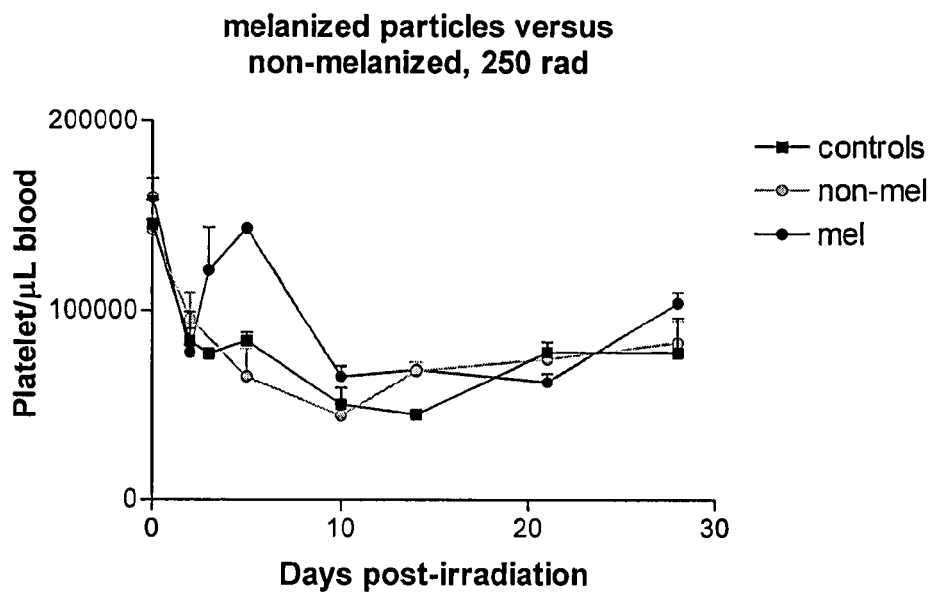
FIG. 11A-11D. Platelet (A, B) and WBC (C, D) counts in mice pre-treated with melanized nanoparticles and irradiated with 2.5 Gy of gamma radiation.
Figure 11B:
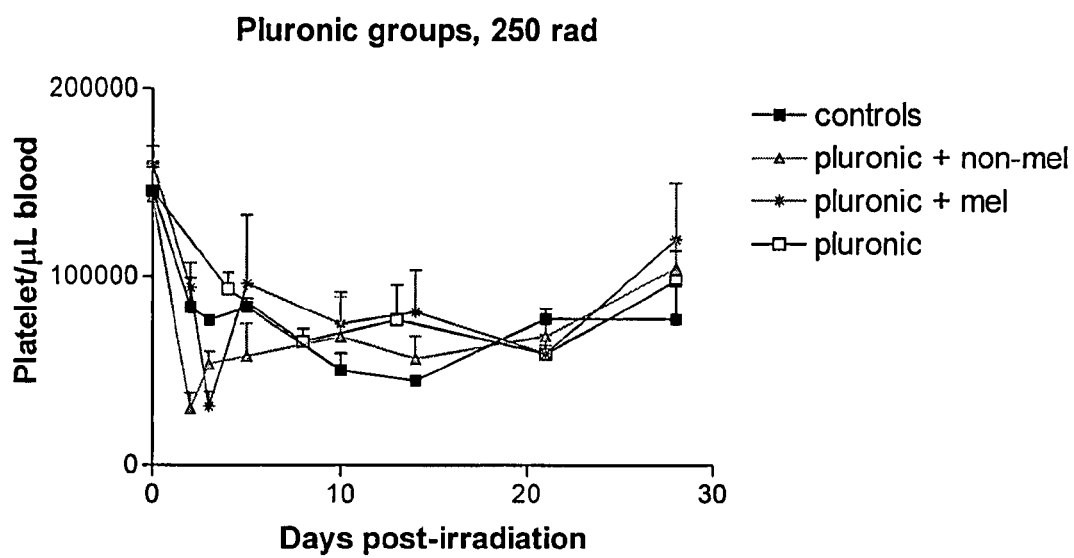
Figure 11C:
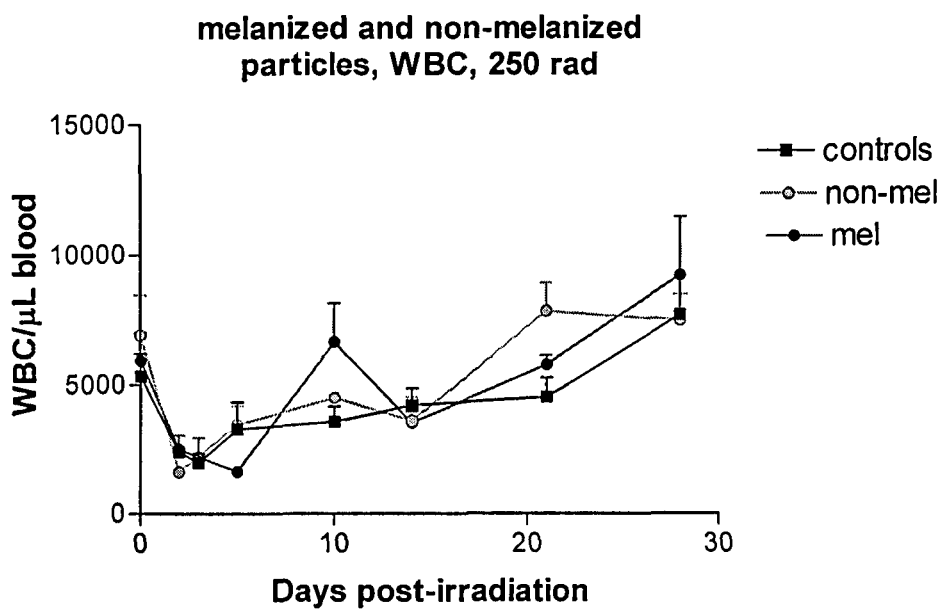
Figure 11D:
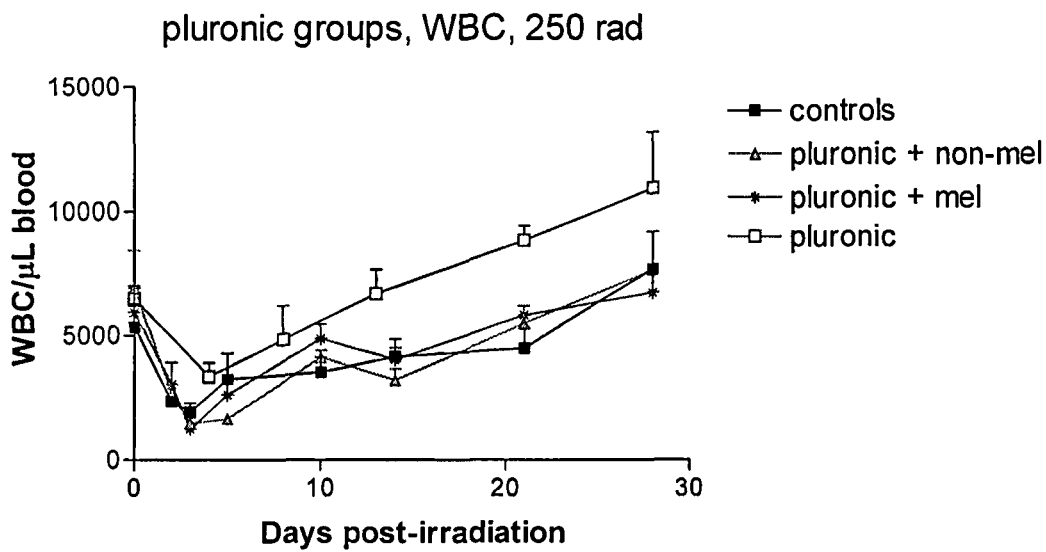

To measure the uptake of melanized particles in major organs and bone marrow with and without a co-polymer of the poloxamer series, melanized particles were radiolabeled with 188-Rhenium ($^{188}Re$) by incubating 16 mg of particles per sample with 40 μL $SnCl_2$ and $Na^{188}ReO_4$ for 2 hr at 37° C., separating the particles from unreacted $Na^{188}ReO_4$ in supernatant by centrifugation, and suspending them in Na carbonate buffer (pH=8.5). Two groups of 4 BALB/c mice were injected IV with 100 μL (1.6 mg, 50 mg/kg body weight) of melanized particles while other two groups of 4 mice were pre-injected IV with 0.13 mg/kg body weight of pluronic acid (pluronic acid F-68 is a member of the poloxamer series, and is available from Sigma as 10% solution) and 12 hr later were injected IV with the above amount of $^{188}Re$-labeled particles. The animals were sacrificed 3 and 24 hr post-injection, their major organs were removed, blotted from blood if necessary, weighed, and their radioactivity was counted in a gamma counter. The results of the biodistribution are presented in FIG. 9. Pre-injection of the animals with pluronic acid significantly (more than 30-fold) increased the uptake of melanized nanoparticles in the bone marrow, thus providing the potential for delivering amounts of nanoparticles sufficient to protect bone marrow from radiation damage. It also should be noted that although liver and spleen, which also take up nanoparticles, are not dose-limiting organs during radiation therapy or radioimmunotherapy, their protection by melanized nanoparticles will be also beneficial, especially in case of radioimmunotherapy when liver and spleen receive significant radiation doses as a result of antibody concentration and metabolism in these organs.

To investigate the radiation protective properties of melanized nanoparticles (MNs), groups of 3 CD-1 mice were injected IV with MNs alone or with pluronic acid (PA)+MNs. Control groups consisted of untreated mice, mice given PA alone, non-melanized nanoparticles alone, and PA+non-melanized nanoparticles. The mice were irradiated with either 1.25 or 2.50 Gy of gamma radiation and their platelet and white blood cell (WBC) counts were monitored for 28 days post-treatment (FIGS. 10-11). The pluronic acid had an immunomodulatory effect by itself but MNs alone clearly provided protection in comparison with control groups on Days 2, 5, 10 and 14 post-treatment. The protective effect was more pronounced in mice irradiated with 1.25 Gy (FIG. 10) than with 2.5 Gy (FIG. 11). Thus, MNs which deposit themselves in bone marrow due to the body "sieving" effect can protect bone marrow against high doses of external gamma radiation, and mouse pre-treatment with PA increases the MNs protective effect. These results are encouraging for the development of similar strategies in patients undergoing EBRT or RIT.

The protective effect of different types of melanin was evaluated on the GI tract in mice receiving lethal dose of 9 Gy at a high dose rate. CD-1 female mice were used in all experiments. Initially a check was made for potential toxicity of synthetic melanin and *C. neoformans* (Cn) melanin "ghosts" made from Cn strain 24067 to the GI track. Mice were fed 15 mg/kg body weight synthetic melanin or ghosts via gavage needle and their body weight and condition were monitored for 30 days. Also, 2 mice out of each group were sacrificed at 24 hr post-feeding with melanin, and their stomachs, small intestine and colon were removed and fixed in formaline-buffered PBS. The parafinized tissues were subsequently cut, stained with H&E and analyzed histologically.

Figure 12:
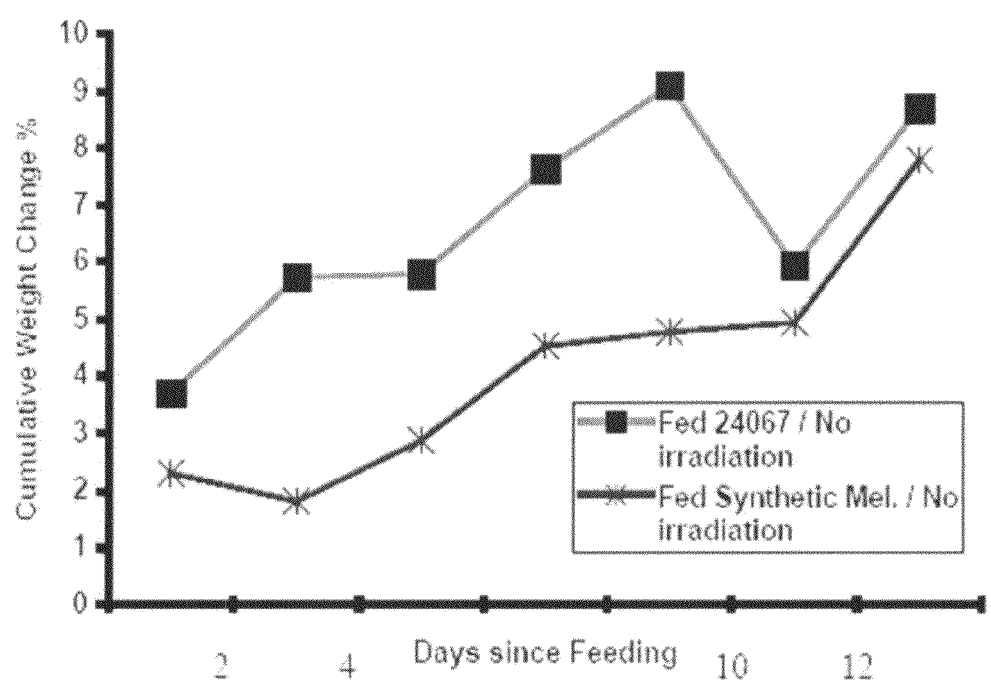
FIG. 12. Body weights of the control CD-1 mice or mice fed with 15 mg/kg body weight synthetic melanin or *C. neoformans* ghosts.
Figures 13A, 13B, 13C:
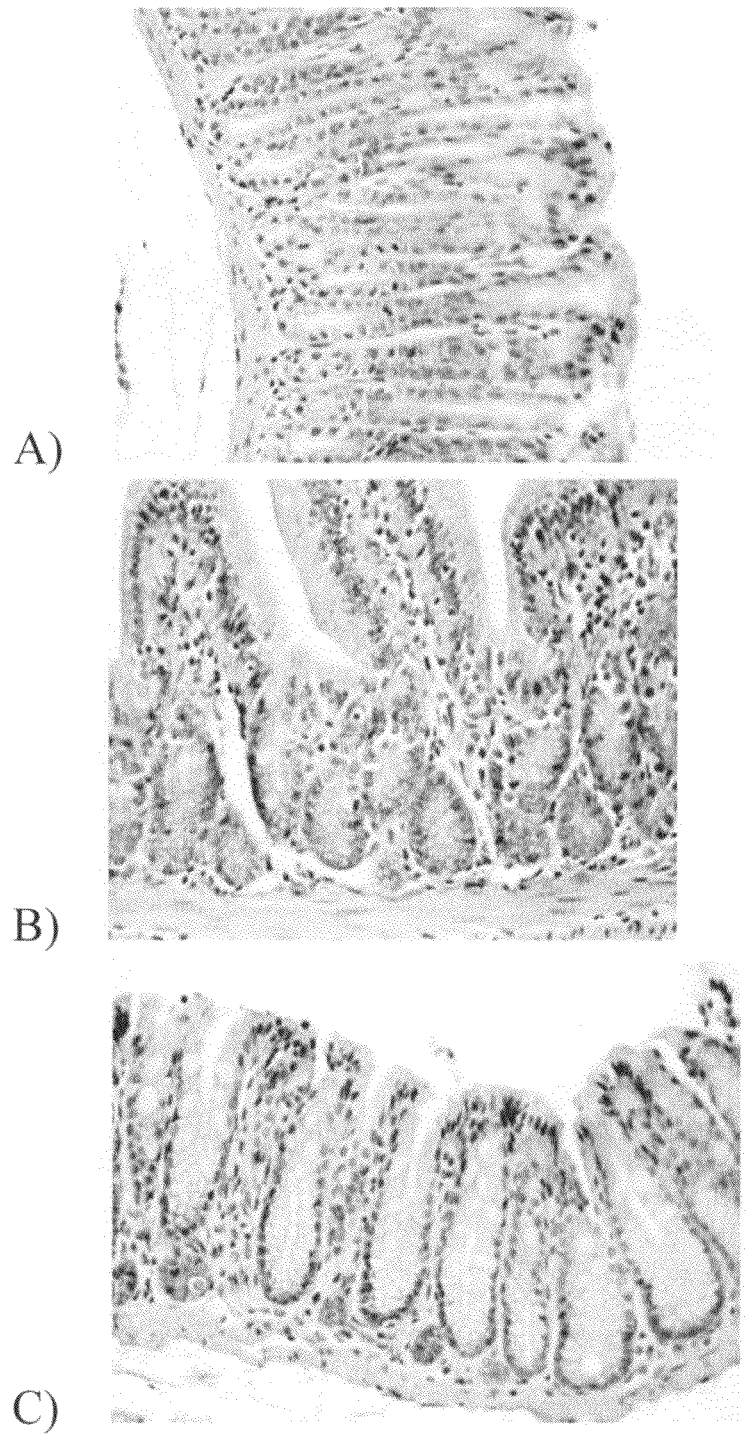
FIG. 13A-13C. Histology of GI organs from CD-1 mice fed with 24067 *C. neoformans* ghosts and sacrificed 24 hr later: A) stomach; B) small intestine; C) colon.

There was no loss in the body weight of melanin-fed mice with all mice consistently gaining weight (FIG. 12). The stomachs, small intestine and colon in mice sacrificed at 24 hr post-feeding were normal (FIG. 13). However, for the first 10 days post-feeding mice given Cn ghosts were gaining more weight which might suggest some inflammation and edema due to immunogenecity of fungal melanin which resolved by day 10. The conclusion from the preliminary experiments was that neither synthetic melanin nor 24067 Cn ghosts were acutely toxic to CD-1 mice in the amount of 15 mg/kg body weight and can be used in radiation protection experiments in vivo.

Figure 14:
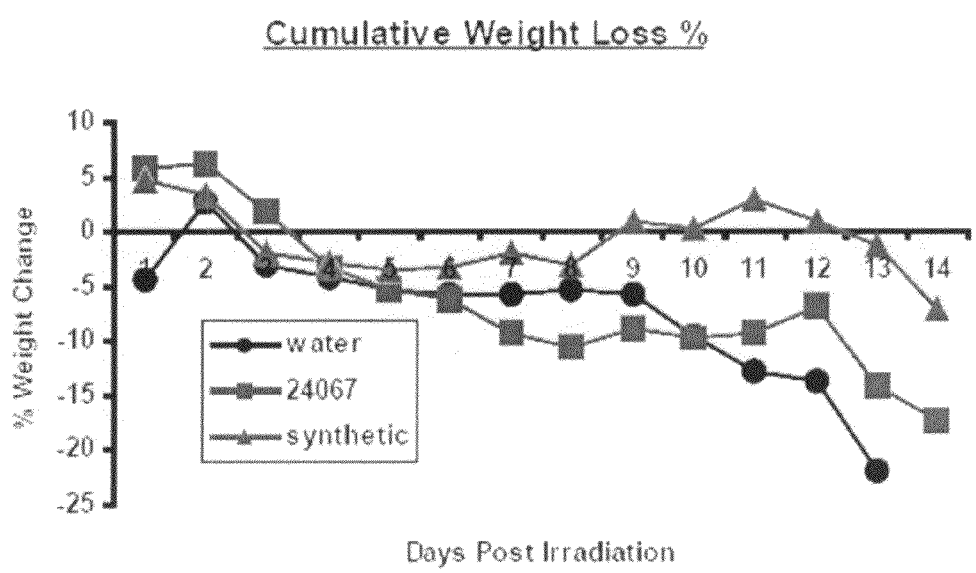
FIG. 14. Cumulative weight loss in CD-1 mice fed with either synthetic melanin of *C. neoformans* ghosts of water (15 mg/kg body weight) and irradiated with 9 Gy whole body dose at 3 Gy/min.
Figure 15:
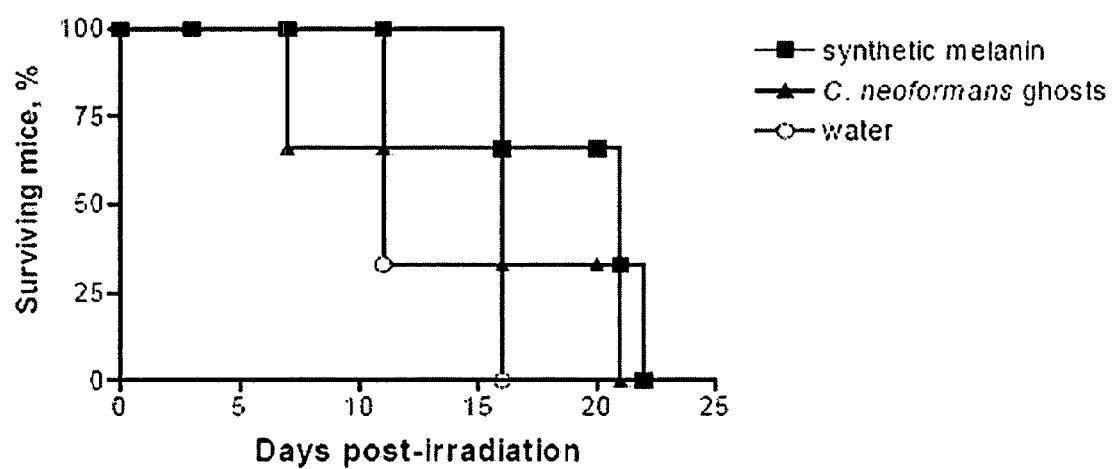
FIG. 15. Survival of mice fed with either synthetic melanin or *C. neoformans* ghosts or water (15 mg/kg body weight) and irradiated with 9 Gy whole body dose at 3 Gy/min.

In the next experiment female CD-1 mice (10 mice per group) were fed 15 mg/kg body weight synthetic melanin or ghosts or water via gavage needle and 1 hr post feeding were subjected to whole body irradiation in 137-Cs irradiator with the total dose of 9 Gy delivered at 3 Gy per min; their body weight and survival were monitored for 22 days. At 4 hr and 24 hr 2 mice per group were sacrificed and their stomachs, small intestine and colon were removed and fixed in formalin-buffered PBS. The parafinized tissues were subsequently cut, stained with H&E and analyzed histologically. For the first 4 days post-irradiation, mice fed with ghosts were loosing less weight than mice fed with either water or synthetic melanin (FIG. 14), which might be explained by some edema accompanying administration of fungal melanin. At day 5 the cumulative weight loss in all groups equalized and for the rest of the observation period the weight loss was the least pronounced in mice fed with synthetic melanin. The overall survival on day 11 post-irradiation was 100% in the synthetic melanin group, 66% in the ghosts group and 33% in control mice fed with water, with the last mouse in this group dying on day 16 (FIG. 15). Mice fed with fungal ghosts survived for 21 days and with synthetic melanin for 22 days, which represents a significant advantage in survival in comparison with the control group. Histological evaluation of GI tissues obtained from mice 4 hr and 24 hr post-irradiation showed that at 4 hr in the stomach of mice fed with ghosts there were fewer apoptotic cells than in stomachs of synthetic melanin or water fed mice (FIG. 16A-C). At 24 hr this trend continued with stomach of mice fed with ghosts having glandular cells which were less vacuolated and attenuated than in the synthetic melanin group) (results not shown). Simultaneously, there were more mitotic figures and less apoptotic cells in both melanin groups in comparison with control water fed mice. In the small intestines there were no difference between the groups with glands of the mucosa showing numerous apoptotic cells. In the colonic glands of mice fed with ghosts there was less cellular reaction and apoptosis as compared to the other colon samples (FIG. 16D-F).

Overall, the prolongation in survival of melanin-fed mice in comparison with control water-fed mice was statistically significant by log-rank test for both synthetic and fungal melanin with synthetic melanin being a better radioprotector in the conditions of experiment. It might be possible that if the ghosts are eliciting inflammation by themselves it could increase the amount of damage sustained from radiation and this could account for less protection with the ghosts than with synthetic melanin. To avoid administration of immunogenic fungal melanin, but to use the advantage of hollow sphere shape which contributes to the radiation scattering by melanin, biodegradable particles of 200-1000 nm diameter made of poly-DL-lactic/glycolic acid (PLGA) polymer from a commercial vendor (Corpuscular Inc, Cold Spring, N.Y.) can be covered with different melanins by incubation in a solution of melanin pre-cursors during autopolymerization as described above and then dissolved the PLGA polymer with the hydrochloric acid. As melanin is extremely resistant to acid, the melanin shell will remain intact while the biodegradable core of the particle will be dissolved. The results of this study indicate that it is possible to utilize melanin for protection of the GI tract from radiation injury.

In summary, the results described herein establish that fungal melanin arranged in nanosize spheres protects against extremely high levels of ionizing radiation and suggest that the protective efficacy of this pigment is a function of its chemical structure, stable free radical presence, and spatial arrangement. In essence, melanin protects against ionizing radiation by mechanisms that are different from the radiation shielding properties of heavy metals, which depend largely on density. These results demonstrate the feasibility of designing low-density nanoshells with radiation shielding properties, which could find uses in a variety of applications by virtue of their low weight. The term "nanoshells" is used to describe nanoparticles of different shapes—e.g., nanospheres, nanotubes, nanoellipsoids and nanorods. Melanin used for manufacturing of nanoshells can be of synthetic or biological origin.

Prophetic Applications

Preparation of additional melanin nanoshells: Melanin-filled nanoshells can be generated by incubating melanin such as *Sepia* melanin in an aerated solution of melanin precursor such as L-dopa or cysteinyl-dopa to provide the conditions for oxidative polymerization as described herein in experiments on generation of melanin-covered nanoparticles for bone marrow protection. To generate melanin-covered nanoshells filled with different materials one can use the above approach with nanoparticles of choice to cover with melanin. For generation of hollow nanospheres, biodegradable nanoparticles made of materials such as proteins or biodegradable plastics will be covered with melanin as above and then treated with concentrated acid which will dissolve the biodegradable nanoparticles but leave the melanin nanoshell intact.

Preparation of melanin-containing plastics: To make plastics impregnated with melanin nanoshells, the melanin nanoshells will be dispersed in a liquid monomer, such as diethylene glycol bis(allyl-carbonate), otherwise know as CR-39, styrene, or methylmethacrylate. Polymerization of the plastic monomer will be initiated with the help of a free-radical initiator. For example, 400 mg benzoyl peroxide will be dissolved in 10 mL of diethylene glycol bis(allyl-carbonate) (CR-39) at 50° C. Then, purified melanin nanoshells will be added, under thorough mixing, in increasing amounts starting from 30 mg until it is possible to form a homogeneous mixture. The mixture will be heated at 50° C. for one day. The mixture will be heated for two additional days at 65° C. under nitrogen, and then cured in a vacuum oven at 110° C. for 2 h.

Incorporation of melanin between two layers of material: Purified melanin nanoshells will be added to a binder/adhesive in the form of a suspension to achieve dispersion of melanin in the binder/adhesive. Then, a hardener will be combined with the binder/adhesive, which will then be immediately "sandwiched" between two layers of material. For example, increasing amounts of purified melanin nanoshells starting from 500 mg will be suspended in 10 mL of chloroform. This suspension will be mixed with 2 mL epoxy resin. The chloroform will then be removed by evaporation leaving melanin homogeneously dispersed in the epoxy resin. Epoxy catalyst, or hardener, will be added, and the mixture will be slowly stirred. Drops of the product will be deposited onto a material such as a plastic or glass, and an identical material will be placed on top of the melanin-epoxy suspension.

Coating surfaces with melanin: As an example, purified melanin nanoshells in increasing amounts starting from 1 g will be suspended in 30 mL of water. Drops of this concentrated melanin suspension will be allowed to spread on the hydrophilized surface of a plastic or glass. The water will be allowed to evaporate leaving melanin attached to the surface of the plastic or glass. As an alternative, a melanin coating may be made on surfaces by first immobilizing on the surface the enzyme laccase which catalyzes melanin formation in fungi. Melanin coated surfaces may also be generated by autopolymerization of melanin precursors. Enzymatically-mediated generation of melanin nanoshells in situ could provide an attractive alternative for coating vulnerable surfaces with this material. Furthermore, since melanin nanoshells are negatively charged, they can be attracted to a surface that is positively charged.

Treatment of buildings to reduce entry of radon and radiation from radon: Radon is a gas that forms naturally during the decay of uranium-238. Radon that occurs naturally in soil can seep from the soil into homes and other buildings. Melanin nanoshells will be added to paints, coatings, and/or building materials. Melanin-based paints and coatings applied to the foundations of buildings, and areas where pipes enter the buildings, can be used for the purpose of trapping radon when it is emitted from rocks or soil before radon enters the building. Radon decays over the course of several days to 210-Pb, which is a beta and gamma emitter and has a half-life of 22 years. Melanin should absorb 210-Pb even tighter than radon through chemosorption as melanin is known to bind two-valent metals and thus should reduce the entry not only of radon but also of radioactive lead into the environment of the building.

Protection of subjects against radiation: A sterile preparation of melanin nanospheres will be injected into an individual at risk for radiation injury. The melanin nanospheres localize to the bone marrow where they provide shielding against the cytotoxic effects of radiation on vulnerable cells. In another application an oral preparation of melanin particles will be ingested to provide protection for the gastrointestinal mucosa. Melanin nanoshells can also be used in protective clothing and gear.

Containment of radioactively contaminated sites: Melanin nanoshells will be used in environmental bioremediation. The following types of radiation are given off by radioactive material: alpha particles, beta particles, x-rays, and gamma rays. The spread of radioactive particles will be reduced by applying the melanin nanoshells to the radioactive particles. Melanin is expected to encapsulate the radioactive particles and thereby reduce their spread. Thus, melanin nanoshells may, for example, prevent the spread of radioactive contamination to ground water. Similarly, melanin nanoshells will be used to contain radiation from radioactive waste and biomedical radioactive materials. Melanin nanoshells may be used in remediation in connection with, for example, waste containers, fuel cladding, packaging containers, transport coverings for all land, air, and water vessels, and nuclear waste clean-up.

Containment of metal ions: Since melanin nanoshells are negatively charged, they may be used to contain positively charged compounds, for example to act as metal chelators and to contain mercury.

Absorption of radiation: Melanin nanoshells may be used to absorb radiation, for example to absorb radar or radiation generated in association with NMR systems.

Industrial, physical buildings and construction: Melanin nanoshells may be used for shielding or containment in buildings, construction and containment structures in connection with, for example, concrete, plastics, steel, titanium, composites, coatings, "wafer" boards or sheeting in walls, roofs, flooring, and conduits. Melanin nanoshells may be used, for example, in shielding in connection with industrial radiation shielding; X-Ray rooms and enclosures (x-rays, gamma radiation); storage and process equipment; airport detection systems (gamma radiation); hot cells (gamma radiation); paints and pigments (alpha and beta particles); glass (alpha particles/radon); power lines (EM radiation/EM field); conductors (EM radiation/EM field); wiring (EM radiation/EM field), transformers (EM radiation/EM field); switches (EM radiation/EM field); meter boxes (EM radiation/EM field); line hardware (EM radiation/EM field); fuses (EM radiation/EM field); breakers (EM radiation/EM field); drywall (alpha particles/radon); plywood (alpha particles/radon); doors (alpha particles/radon); door frames (alpha particles/radon), window frames (alpha particles/radon); granite (alpha particles/radon); concrete (alpha particles/radon); ceramic materials (tile); commercial fertilizers (alpha particles/radium); angles (alpha particles/radon); pigs (alpha particles/radon); castings (alpha particles/radon); heat lamps (infrared radiation, UV light); road construction materials; pipes and colts (alpha particles/radon); heaters (infrared radiation); radio wave transmitters (EM radiation/radio waves); industrial radiographers (x-ray and gamma radiation); roof tiles (alpha particles/radon); metal (alpha particles/radon); steel (alpha particles/radon); titanium (alpha particles/radon); stucco (alpha particles/radon); caulk (alpha particles/radon); plastic (all types of radiation); mortar (alpha particles/radon); brick (alpha particles/radon); and VDUs (Vacuum Distillation units) (all types of radiation). This includes the use of melanin nanoshells in fossil-fuel power plants, chemical plants, paper plants, etc. and clean-up/binding of mercury and other toxic release inventory (TRI) gases/metals emissions.

Operational Equipment: Melanin nanoshells may be used for shielding and containment in composites, coatings, or inserts in equipment with radiation exposure; for pressurized water reactors (PWRs), equipment on primary sides of plant, including, but not limited to, reactor core, reactor vessel, steam generators, pumps, conduit, electrical relay boxes; and in boiling water reactors (BWRs), primary side equipment including boilers, pumps, conduits, and also secondary side equipment including turbines, condensers, pumps, relays, and generators where radiation exists.

Airlines: Melanin nanoshells may be used in shielding in air craft in connection with, for example, airplane materials (windows, cockpit gauges, mechanical parts, etc.) (cosmic radiation); cabinet X-ray system (x-rays); human X-ray scanner (x-rays); and blimps (cosmic radiation).

Space: Melanin nanoshells may be used for shielding and containment in space craft in connection with, for example, astronaut jumpsuits (galactic cosmic radiation), spacecraft parts (galactic cosmic radiation), and rocket parts (engines, turbines, etc.) (galactic cosmic radiation).

Vehicles: Melanin nanoshells may be used for shielding and containment in connection with, for example, ship parts (hull, engines, motor, etc.), vehicle parts, gauges (beta particles/tritium), and alternate fuel sources (e.g. nuclear energy).

Defense Application: Melanin nanoshells may be used for shielding and containment in defense applications in connection with, for example, helicopter materials (cosmic radiation); submarine materials (alpha particles, beta particles, x-rays, and gamma radiation); navy carrier parts (alpha particles, beta particles, x-rays, and gamma radiation); fighter jet parts (cosmic radiation); tank parts (alpha particles, beta particles, x-rays, and gamma radiation); naval nuclear propulsion (alpha particles, beta particles, x-rays, and gamma radiation); nuclear powered vehicles; and weapon night sights (e.g., night vision goggles) (beta particles/tritium; infrared radiation). Other applications include use of melanin nanoshells in radar elusion in manned and unmanned vehicles.

Nuclear Application: Radioactive materials in nuclear applications give off the following types of radiation: alpha particles, beta particles, x-rays, gamma rays, neutrons, protons, and heavy ions. Melanin nanoshells may be used for shielding and containment in nuclear applications in connection with, for example, power plant building materials, decay drums, waste containers, power reactors, pressurized water reactors, plant building materials, reactor core, reactor vessel, steam generators, steam turbines, pumps, electrical relay boxes, conduits, boiling water reactors, boilers, pumps, condensers, relays, respirators, neutron generators, nuclear fuel reprocessors, master-slave manipulators, nuclear batteries, radiation fallout material, and tools, gear, and equipment. In radioactive material or waste storage, including spent fuel storage, melanin nanoshells may be used for shielding and containment in building material, equipment, and fuel cladding. In transport of radioactive material or waste, melanin nanoshells may be used for shielding and containment in packaging, containers, trucks/railcars/planes/water vessels, and covering/coating/composites. In radiation contamination clean-up, melanin nanoshells may be used for stabilizing radioactive isotopes in clean-up conditions.

Homeland security: Melanin nanoshells may be used for shielding and containment in homeland security applications in connection with, for example, protection of buildings, equipment, computers, satellites, etc. and protection of masses of people through clothing applications, house shielding, etc. from nuclear or "dirty" bombs.

Medical/dental: Melanin nanoshells may be used for shielding and containment in medical and dental applications in connection with, for example, MRI machines (gamma radiation); X-Ray machines (gamma radiation); mammogram machines (gamma radiation); lasers (infrared radiation); dental crowns (gamma radiation/uranium); PET Scans (beta particles); dental porcelains (gamma radiation/uranium/thorium); external-beam radiation therapy machines (used to target localized areas of a tumor) (gamma radiation, electron beams, neutron and heavy ion beams); X-ray Tubes (gamma radiation); lab coats, coveralls, and head covers; sterilizers (gamma radiation/cobalt-60); sonogram machines (gamma radiation); radiopharmaceuticals (injectable radioisotopes) (gamma, alpha, beta (both positive and negative) and Auger electron radiation); medical diagnostic imaging; cardiac cath swing lab shielded partitions (gamma radiation); and nuclear medicine products (gamma, alpha, beta (both positive and negative) and Auger electron radiation). In medical radiation therapy, melanin nanoshells may be used in coatings to protect, for example, the following against x-ray and gamma radiation: linear accelerator swinging door systems, linear accelerator sliding door systems, H.D.R. automated swing door systems, gamma knife door systems, H.V.A.C. shielding systems, H.D.R. treatment enclosures, treatment room shielding upgrade systems, square-edge and interlocking bricks, modular vault systems, and proton therapy shielding systems.

Science Labs: Melanin nanoshells may be used in shielding in science laboratories in connection with, for example, anodes (x-rays), atomic particle accelerators (x-rays, UV radiation), X-Ray diffraction units (x-rays), and electron microscopes (EM radiation, x-rays, and beta particles).

Consumer products: Melanin nanoshells may be used in shielding in consumer products in connection with, for example, protective clothes, shoes, sunglasses (EM radiation/UV light), eye glasses (EM radiation/UV light), contacts (EM radiation/UV light), make-up (EM radiation/UV light), lip gloss (EM radiation/UV light), ovens (alpha particles), toaster ovens (alpha particles), cell phone and covers (EM radiation/radio waves), televisions (alpha particles, extremely low frequency EM fields, x-rays), watches (beta particles/tritium), glow in the dark products (beta particles), light bulbs (UV radiation, infrared radiation), fire alarms (alpha particles), smoke detectors (alpha particles/americium-241, low energy gamma radiation), emergency exit signs (beta particles, tritium), tobacco (alpha particles), wireless technology, water fountains (alpha particles, radon), lantern mantles (alpha, beta, and gamma particles), lamp starters (beta particles, tritium, promethium, gamma particles, thorium), static eliminators (alpha particles/polonium-210), compasses (beta particles), batteries (beta particles/tritium), pagers (EM radiation), generators, purses, hats, gloves, shampoo and conditioner (EM radiation/UV light), hair spray (EM radiation/UV light), CRT (cathode-ray tube) monitors (x-rays), tanning bed goggles (EM radiation/UV light), cable tv wires (EM radiation), hair dryers (infrared radiation), pottery glaze (alpha, beta, and gamma particles), and food packaging materials.

Energy production, transmission and distribution: Melanin nanoshells may be used in connection with, for example, coating/composites on conductors and wiring to reduce/avoid electromagnetic field (EMF) radiation and line current losses, and coating/composites/inserts into electrical equipment and electrical working tools including, but not limited to, transformers (all sizes and types), switches, meter boxes, line hardware, fuses, and breakers, etc.

REFERENCES

1. Hill, H. Z. The function of melanin or six blind people examine an elephant. *Bioessays* 14: 49-56 (1992).
2. Wang, Y., Aisen, P., and Casadevall, A. Melanin, melanin "ghosts" and melanin composition in *Cryptococcus neoformans*. *Infec. Immun.* 64: 2420-2424 (1996).

3. Steenbergen, J. N., Shuman, H. A., Casadevall, A. *Cryptococcus neoformans* interactions with amoebae suggest an explanation for its virulence and intracellular pathogenic strategy in macrophages. *Proc. Natl. Acad. Sci. USA*. 98: 15245-15250 (2001).
4. Nosanchuk, J. D. and Casadevall, A. The contribution of melanin to microbial pathogenesis. *Cell. Microbiol.* 5: 203-223 (2003).
5. Mirchink, T. G., Kashkina, G. B., Abaturov, Iu. D. Resistance of fungi with different pigments to radiation. *Mikrobiologiia* 41: 83-86 (1972).
6. Mironenko, N. V., Alekhina, I. A., Zhdanova, N. N. & Bulat, S. A. Intraspecific variation in gamma-radiation resistance and genomic structure in the filamentous fungus *Alternaria alternata*: a case study of strains inhabiting Chernobyl reactor no. 4. *Ecotoxicol. Environ. Saf.* 45: 177-187 (2000).
7. Vasilevskaia, A. I., Zhdanova, N. N., & Gavriliuk, V. I. The dynamics of the fungal mycelial content in the soils of stationary posts in a 30-kilometer zone around the Chernobyl Atomic Electric Power Station *Mikrobiol. Z.* 55: 8-15 (1993).
8. Sinilova, N. G., Pershina, Z. G., Duplitseva, A. P., Pavlova, I. B. A radioresistant pigmented bacterial culture isolated from atomic reactor water. *Zh Mikrobiol Epidemiol Immunobiol.* 46: 94-99 (1969).
9. Rofstad E K. Radiation biology of malignant melanoma. *Acta Radiol Oncol* 25: 1-10, 1986.
10. Della-Cioppa, G. R., Garger, Jr. S. J., Holtz, R. B., McCulloch, M. J., Sverlow, G. G. Method for making stable extracellular tyrosinase and synthesis of polyphenolic polymers therefrom. U.S. Pat. No. 5,801,047.
11. Dadachova, E., Howell, R. W., Bryan, R. A., Frenkel, A., Nosanchuk, J. D., Casadevall, A. Susceptibility of human pathogens *Cryptococcus neoformans* and *Histoplasma capsulatum* to gamma radiation versus radioimmunotherapy with alpha- and beta-emitting radioisotopes. *J. Nucl. Med.* 45: 313-320 (2004).
12. Hall, E. J., *Radiobiology for the Radiologist* (Lippincott Williams & Willkins, Philadelphia), p. 91-94 (2000).
13. Yong, M. E. J. *Radiological Physics*, Charles C. Thomas, Springfield, Ill. p. 171-204, 1967.
14. Wilczok, T., Bilinska, B., Buszman, E., Kopera, M. Spectroscopic studies of chemically modified synthetic melanins. *Arch. Biochem. Biophys.* 231: 257-262 (1984).
15. d'Ischia M, Prota G. Photooxidation of 5,6-dihydroxy-1-methyl-indole. *Tetrahedron* 43: 431-434 (1987).
16. Ito, S., Fujita, K. Microanalysis of eumelanin and pheomelanin in hair and melanomas by chemical degradation and liquid chromatography. *Anal. Biochem.* 144: 527-536 (1985).
17. Wakamatsu, K, Ito, S. Advanced chemical methods in melanin determination. *Pigment Cell Res.* 15: 174-183 (2003).
18. Liu, L., Wakamatsu, K., Ito, S., Williamson, P. R. Catecholamine oxidative products, but not melanin, are produced by *Cryptococcus neoformans* during neuropathogenesis in mice. *Infect. Immun.* 67: 108-112 (1999).
19. Morris, P. R., Terreni, A. A., DiSalvo, A. F. Red-pigmented *Histoplasma capsulatum*—an unusual variant. *J. Med. Vet. Mycol.* 24: 231-233 (1986).
20. Rosas A L et al Isolation and serological analyses of fungal melanins. *J Immunol Meth* 244: 69-80 (2000).
21. Enochs, W. S., Nilges, M. J. and Swartz, H. M. The standardized test for the identification and characterization of melanins using electron paramagnetic (EPR) spectroscopy. *Pigment Cell Res.* 6: 91-99 (1993).
22. Sorenson J A, Phelps M E. *Physics in Nuclear Medicine*. WB Saunders Co., Philadelphia 1987.
23. Dadachova E., Nosanchuk J. D., Shi L., Schweitzer A. D., Frenkel A., Nosanchuk J. S. and Casadevall A. Dead cells in melanoma tumors provide abundant antigen for targeted delivery of ionizing radiation by a mAb to melanin, Proc Natl Acad Sci USA (2004) Oct. 12; 101(41):14865-70. Epub 2004 Oct. 5.
24. Porter C J, Moghimi S M, Illum L, Davis S S. The polyoxyethylene/polyoxypropylene block co-polymer poloxamer-407 selectively redirects intravenously injected microspheres to sinusoidal endothelial cells of rabbit bone marrow. FEBS Lett. 305(1):62-6 (1992).
25. Moghimi S M. Prolonging the circulation time and modifying the body distribution of intravenously injected polystyrene nanospheres by prior intravenous administration of poloxamine-908. A 'hepatic-blockade' event or manipulation of nanosphere surface in vivo? Biochim Biophys Acta. 1336(1):1-6 (1997).
26. Nosanchuk, J. D., Rosas, A. L., Casadevall. A. The antibody response to fungal melanin in mice. J. Immunol. 160:6026-6031 (1998).
27. Moghimi S M, Hunter A C. Capture of stealth nanoparticles by the body's defenses. Crit Rev Ther Drug Carrier Syst. 18(6):527-50 (2001).
28. Moghimi S M, Pavey K D, Hunter A C. Real-time evidence of surface modification at polystyrene lattices by poloxamine 908 in the presence of serum: in vivo conversion of macrophage-prone nanoparticles to stealth entities by poloxamine 908. FEBS Lett. 2003 Jul. 17; 547(1-3): 177-82.
29. Bonner, T. G., A. Duncan. 1962. Infra-red spectra of some melanins. *Nature* 194:1078-1079.
30. Jacobson, E. S. 2000. Pathogenic roles for fungal melanins. *Clin. Microbiol. Rev.* 13:708-717.
31. Chaskes, S. and R. L. Tyndall. 1975. Pigment production by *Cryptococcus neoformans* from para- and ortho-diphenols: effect of the nitrogen source. *J. Clin. Microbiol.* 1:509-514.
32. Chaskes, S. and R. L. Tyndall. 1978. Pigment production by *Cryptococcus neoformans* and other *Cryptococcus* species from aminophenols and diaminobenzenes. *J. Clin. Microbiol.* 7:146-152.
33. Chaskes, S. and R. Tyndall. 1978. Pigmentation and autoflourescence of *cryptococcus* species after growth on tryptophan and anthranilic acid media. *Mycopathologia* 64:105-112.

What is claimed is:

1. A method for protecting bone marrow of a subject from radiation during radiation therapy comprising systemically administering to the subject prior to radiation therapy a radioprotective amount of nanoparticles comprising melanin to protect the bone marrow of the subject from radiation during radiation therapy, wherein the nanoparticles are administered in a manner effective to be taken up by the bone marrow and wherein the radiation is delivered at a rate of at least 3 Gy per minute.

2. The method of claim 1, wherein the nanoparticles comprise polymerized L-dopa, epinephrine, methyldopa and/or a phenol that polymerizes into melanin.

3. The method of claim 1, wherein the nanoparticles comprise melanin isolated or derived from a biological source or generated by chemical synthetic process.

4. The method of claim 3, wherein the biological source is a plant, an animal, or a melanin-containing fungus, bacterium or cell.

5. The method of claim 4, wherein the fungus is *Cryptococcus neoformans* and/or *Histoplasma capsulatum*.

6. The method of claim 1, wherein the melanin consists of pheomelanin.

7. The method of claim 1, wherein the nanoparticles comprise pheomelanin and eumelanin and wherein the ratio of pheomelanin to eumelanin is at least 1:1.

8. The method of claim 1, wherein the melanin contains divalent sulphur.

9. The method of claim 1, wherein the nanoparticles comprise a nanosphere, a nanotube, a nanoellipsoid, a nanoball and/or a nanorod.

10. The method of claim 1, wherein the nanoparticles have a thickness of about 10 nm to about 1,000 nm.

11. The method of claim 1, further comprising protecting the subject's liver, spleen, kidneys, lungs, or gastrointestinal tract from radiation.

12. The method of claim 1, wherein the radiation therapy is radioimmunotherapy.

13. The method of claim 1, wherein the radiation therapy is external beam radiation therapy.

14. The method of claim 1, which further comprises administering to the subject a co-polymer of the poloxamer series.

15. The method of claim 14, wherein the co-polymer of the poloxamer series is pluronic acid.

16. The method of claim 14, wherein the co-polymer of the poloxamer series is administered to the subject prior to administering the nanoparticles.

17. The method of claim 1, wherein the nanoparticles comprising melanin are silica nanoparticles covered with a layer comprising melanin.

18. The method of claim 1, and wherein the radiation is delivered at a rate of at least 14 Gy per minute.

* * * * *